United States Patent [19]
Baker et al.

[11] Patent Number: 5,696,156
[45] Date of Patent: Dec. 9, 1997

[54] TRITERPENE DERIVATIVES WITH IMMUNOSUPPRESSANT ACTIVITY

[75] Inventors: Robert K. Baker, Cranford; Frank Kayser, Hoboken; Jianming Bao, Westfield; William H. Parsons, Belle Mead; Kathleen M. Rupprecht, Cranford, all of N.J.

[73] Assignee: Merck & Co. Inc., Rahway, N.J.

[21] Appl. No.: 733,037

[22] Filed: Oct. 16, 1996

Related U.S. Application Data

[60] Provisional application No. 60/008,169 Oct. 31, 1995 and No. 60.008,189 Oct. 31, 1995.

[51] Int. Cl.$^6$ .................. A61K 31/365; C07D 313/06
[52] U.S. Cl. .................. 514/450; 549/268; 549/354
[58] Field of Search .................. 549/268, 354; 514/450

[56] References Cited

FOREIGN PATENT DOCUMENTS

WO 96/40688  12/1996  WIPO .

OTHER PUBLICATIONS

Abreu, et al., "A Nor–Triterpenoid from Lophanthera Lactescens.", Phytochemistry, vol. 29(7), pp. 2257–2261, 1990.

*Primary Examiner*—Bernard Dentz
*Attorney, Agent, or Firm*—Valerie J. Camara; Mark R. Daniel

[57] ABSTRACT

The compounds of Formula I

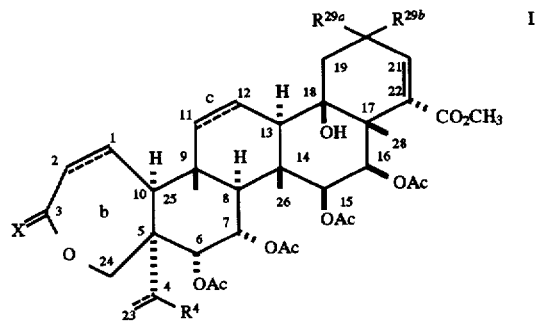

are useful as immunosuppressive agents.

19 Claims, No Drawings

TRITERPENE DERIVATIVES WITH IMMUNOSUPPRESSANT ACTIVITY

RELATED APPLICATIONS

This application claims benefit of U.S. Provisional application Ser. Nos. 60/008,169 and 60/008,189, both filed on Oct. 31, 1995.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort.

Newer, safer drugs exhibiting less side effects are constantly being searched for in the field.

Four active components of *Spachea correa* were recently identified which inhibit thymidine uptake of T cells and are useful as immunosuppressive agents in animals, including man.

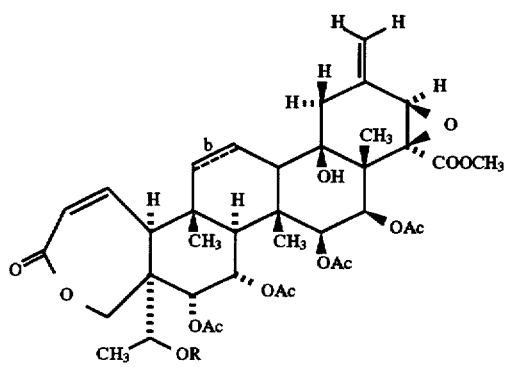

Formula 1(a)b is a single bond and R is OAc
Formula 1(b)b is a double bond and R is OAc
Formula 1(c)b is a single bond and R is OH
Formula 1(d)b is a double bond and R is OH These compounds are useful as immunosuppressive agents in animals, including man. The present invention describes newly developed immunosuppressive compounds derived from the compounds described in Formulae 1(a) through 1(d) and which have the relative stereochemistry depicted above.

SUMMARY OF THE INVENTION

This invention relates to a class of triterpene derivatives of the general structural Formula I

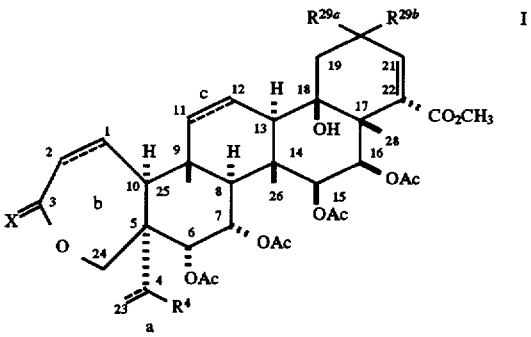

are useful as immunosuppressives.

As an immunosuppressive, the compounds of this invention are useful in the treatment of autoimmune diseases, the prevention of rejection of foreign organ transplants and/or related afflictions, diseases and illnesses. Also within the scope of this invention are pharmaceutical formulations comprising a compound of Formula I and a pharmaceutical carrier, as well as, pharmaceutical formulations comprising a compound of Formula I, a second immunosuppressive agent and a pharmaceutical carrier.

DETAILED DESCRIPTION OF THE INVENTION

A. Scope of the Invention

The present invention is related to compounds of formula I, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fasciitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins), lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis sclerosing cholangitis), partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

More particularly, this invention relates to compounds of the general structural formula I:

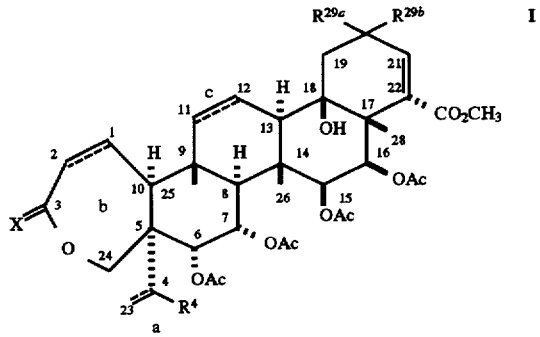

or a pharmaceutically acceptable salt, crystal form, or hydrate, wherein:

X is: O, S, NH or H and $R^1$;

a is: a single bond, or a double bond when $R^4$ is absent;

b and c are independently: a single bond or a double bond;

n is: 1 to 4;

m is: 1 to 4;

r is: 0 or 1;

s is: 0 or 1;

$R^1$ and $R^2$ are independently:
  a) H, or
  b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR_1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR_1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR_1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
  a) —$(C_1-C_6)$-alkyl, alkyl as defined above;
  b) —$(C_1-C_6)$-alkenyl, wherein alkenyl is unsubstituted or substituted with one, two or three substituents selected from the group consisting of: Br, Cl, F, I, ($C_1$-$C_6$)-alkoxy, cyano, oxo, nitro, hydroxy, CHO, $CO_2H$, $COC_1$-$C_6$-alkyl, $CO_2C_1$-$C_6$-alkyl, $CONR^1R^2$, $NR^1R^2$, $NR_1COC_1$-$C_6$-alkyl, aryl as defined above, and heteroaryl as defined above;

c) —($C_1$-$C_6$)-alkynyl, wherein alkynyl is unsubstituted or substituted with one, two or three substituents selected from the group consisting of: Br, Cl, F, I, ($C_1$-$C_6$)-alkoxy, cyano, oxo, nitro, hydroxy, CHO, $CO_2H$, $COC_1$-$C_6$-alkyl, $CO_2C_1$-$C_6$-alkyl, $CONR^1R^2$, $NR^1R^2$, $NR_1COC_1$-$C_6$-alkyl, aryl as defined above, and heteroaryl as defined above, d) -aryl, aryl as defined above, or e) -heteroaryl, heteroaryl as defined above;

$R^4$ is:

a) absent and a is a double bond;
b) —H,
c) —OH,
d) =O,
e) —O[(C=O)$O_r$]$_s$$C_1$-$C_{10}$-alkyl, alkyl as defined above,
f) —O[(C=O)$O_r$]$_s$$C_2$-$C_{10}$-alkenyl, as defined above,
g) —O[(C=O)$O_r$]$_s$$C_2$-$C_6$-alkynyl, alkynyl as defined above,
h) —O[(C=O)$O_r$]$_s$($C_3$-$C_7$)-cycloalkyl,
i) —O[(C=O)$O_r$]$_s$aryl, aryl as defined above,
j) —O[(C=O)$O_r$]$_s$heteroaryl, heteroaryl as defined above,
k) —O($CH_2$)$_n$O($CH_2$)$_m$heteroaryl, heteroaryl as defined above,
l) —O($CH_2$)$_n$O($CH_2$)$_m$aryl, aryl as defined above,
m) —OC(=O)$NR^1R^2$,
n) —$OSO_2R^3$, or
o) —$NR^1R^2$;

$R^{29a}$ and $R^{29b}$ are independently:

a) —H,
b) =O,
c) —($CH_2$)$_s$—O[(C=O)$O_r$]$_s$$C_1$-$C_{10}$-alkyl, alkyl as defined above,
d) —($CH_2$)$_s$—O[(C=O)$O_r$]$_s$$C_2$-$C_{10}$-alkenyl, alkenyl as defined above,
e) —($CH_2$)$_s$—O[(C=O)$O_r$]$_s$$C_2$-$C_6$-alkynyl, alkynyl as defined above,
f) —($CH_2$)$_s$—O[(C=O)$O_r$]$_s$($C_3$-$C_7$)-cycloalkyl,
g) —($CH_2$)$_s$—O[(C=O)$O_r$]$_s$aryl, aryl as defined above,
h) —($CH_2$)$_s$—O[(C=O)$O_r$]$_s$heteroaryl, heteroaryl as defined above,
i) —($CH_2$)$_s$—O($CH_2$)$_n$O($CH_2$)$_m$heteroaryl, heteroaryl as defined above,
j) —($CH_2$)$_s$—O($CH_2$)$_n$O($CH_2$)$_m$aryl, aryl as defined above,
k) —($CH_2$)$_s$—OC(=O)$NR^1R^2$,
l) —($CH_2$)$_s$—$OSO_2R^3$,
m) —($C_1$-$C_6$)-alkyl, alkyl as defined above,
n) —($C_2$-$C_6$)-alkenyl, alkenyl as defined above, or
o) =C($C_1$-$C_{10}$-alkyl)$_2$, alkyl as defined above.

An embodiment of the invention are the compounds of Formula I

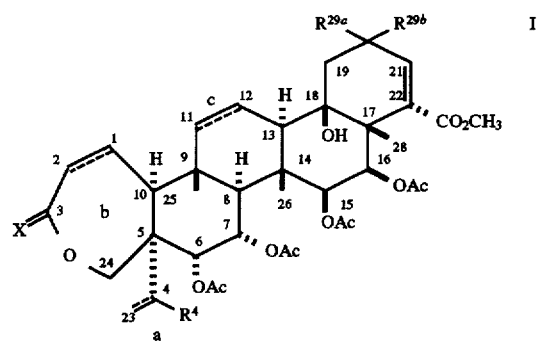

or a pharmaceutically acceptable salt, crystal form, or hydrate, wherein:

X is: O, S, or NH;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:

a) H, or
b) ($C_1$-$C_6$)-alkyl, wherein alkyl is unsubstituted or substituted with one, two or three substituents selected from the group consisting of: Br, Cl, F, I, ($C_1$-$C_6$)-alkoxy, vinyl, cyano, oxo, nitro, hydroxy, CHO, $CO_2H$, $COC_1$-$C_6$-alkyl, $CO_2C_1$-$C_6$-alkyl, $CONR^1R^2$, $NR^1R^2$, $NR^1COC_1$-$C_6$-alkyl, aryl, wherein aryl is defined as phenyl or naphthyl, unsubstituted or substituted with one, two or three substituents selected from the group consisting of: Br, Cl, F, I, ($C_1$-$C_6$)-alkoxy, phenyl, phenoxy, cyano, nitro, hydroxy, CHO, $CO_2H$, $COC_1$-$C_6$-alkyl, $CO_2C_1$-$C_6$-alkyl, $CONR^1R^2$, $NR^1R^2$, $NR^1COC_1$-$C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$-$C_6$)-alkoxy, cyano, nitro, hydroxy, CHO, $CO_2H$, $COC_1$-$C_6$-alkyl, $CO_2C_1$-$C_6$-alkyl, $CONR^1R^2$, $NR^1R^2$, $NR^1COC_1$-$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:

a) —($C_1$-$C_6$)-alkyl, alkyl as defined above;
b) —($C_1$-$C_6$)-alkenyl, wherein alkenyl is unsubstituted or substituted with one, two or three substituents selected from the group consisting of: Br, Cl, F, I, ($C_1$-$C_6$)-alkoxy, cyano, oxo, nitro, hydroxy, CHO, $CO_2H$, $COC_1$-$C_6$-alkyl, $CO_2C_1$-$C_6$-alkyl, $CONR^1R^2$, $NR^1R^2$, $NR^1COC_1$-$C_6$-alkyl, aryl as defined above, and heteroaryl as defined above;
c) —($C_1$-$C_6$)-alkynyl, wherein alkynyl is unsubstituted or substituted with one, two or three substituents selected from the group consisting of: Br, Cl, F, I, ($C_1$–$C_6$)-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)O$_r$]$_s$$C_1$–$C_{10}$-alkyl, alkyl as defined above,
f) —O[(C=O)O$_r$]$_s$$C_2$–$C_{10}$-alkenyl, as defined above,
g) —O[(C=O)O$_r$]$_s$$C_2$–$C_6$-alkynyl, alkynyl as defined above,
h) —O[(C=O)O$_r$]$_s$($C_3$–$C_7$)-cycloalkyl,
i) —O[(C=O)O$_r$]$_s$aryl, aryl as defined above,
j) —O[(C=O)O$_r$]$_s$heteroaryl, heteroaryl as defined above,
k) —O($CH_2$)$_n$O($CH_2$)$_m$heteroaryl, heteroaryl as defined above,
l) —O($CH_2$)$_n$O($CH_2$)$_m$aryl, aryl as defined above,
m) —OC(=O)$NR^1R^2$,
n) —O$SO_2R^3$, or
o) —$NR^1R^2$; and $R^{29a}$ and $R^{29b}$ are independently:
a) —H,
b) =O,
c) —($CH_2$)$_s$—O[(C=O)O$_r$]$_s$$C_1$–$C_{10}$-alkyl, alkyl as defined above,
d) —($CH_2$)$_s$—O[(C=O)O$_r$]$_s$$C_2$–$C_{10}$-alkenyl, alkenyl as defined above,
e) —($CH_2$)$_s$—O[(C=O)O$_r$]$_s$$C_2$–$C_6$-alkynyl, alkynyl as defined above,
f) —($CH_2$)$_s$—O[(C=O)O$_r$]$_s$($C_3$–$C_7$)-cycloalkyl,
g) —($CH_2$)$_s$—O[(C=O)O$_r$]$_s$aryl, aryl as defined above,
h) —($CH_2$)$_s$—O[(C=O)O$_r$]$_s$heteroaryl, heteroaryl as defined above,
i) —($CH_2$)$_s$—O($CH_2$)$_n$O($CH_2$)$_m$heteroaryl, heteroaryl as defined above,
j) —($CH_2$)$_s$—O($CH_2$)$_n$O($CH_2$)$_m$aryl, aryl as defined above,
k) —($CH_2$)$_s$—OC(=O)$NR^1R^2$,
l) —($CH_2$)$_s$—O$SO_2R^3$,
m) —($C_1$–$C_6$)-alkyl, alkyl as defined above,
n) —($C_2$–$C_6$)-alkenyl, alkenyl as defined above, or
o) =C($C_1$–$C_{10}$-alkyl)$_2$, alkyl as defined above.

An embodiment of this embodiment of the invention are the compounds of Formula I

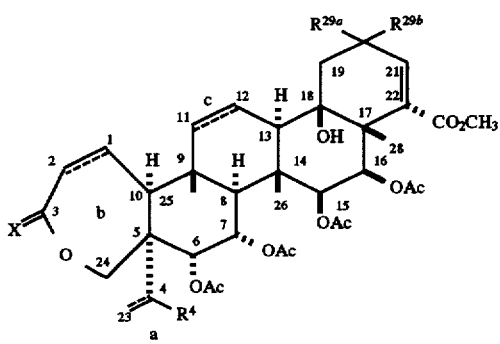

or a pharmaceutically acceptable salt, crystal form, or hydrate, wherein:

X is: O;
a is: a single bond;
b and c are independently: a single bond or a double bond;
n is: 1 to 4;
m is: 1 to 4;
r is: 0 or 1;
s is: 0 or 1;

$R^1$ and $R^2$ are independently:
a) H, or
b) ($C_1$–$C_6$)-alkyl, wherein alkyl is unsubstituted or substituted with one, two or three substituents selected from the group consisting of: Br, Cl, F, I ($C_1$–$C_6$)-alkoxy, vinyl, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —($C_1$–$C_6$)-alkyl, alkyl as defined above,
b) -aryl, aryl as defined above, or
c) -heteroaryl, heteroaryl as defined above;

$R^4$ is:
a) —O[(C=O)O$_r$]$_s$$C_1$–$C_{10}$-alkyl, alkyl as defined above,
b) —O[(C=O)O$_r$]$_s$($C_3$–$C_7$)-cycloalkyl,
c) —O[(C=O)O$_r$]$_s$aryl, aryl as defined above,
d) —O[(C=O)O$_r$]$_s$heteroaryl, heteroaryl as defined above,
e) —O($CH_2$)$_n$O($CH_2$)$_m$heteroaryl, heteroaryl as defined above,
f) —O($CH_2$)$_n$O($CH_2$)$_m$aryl, aryl as defined above,
g) —OC(=O)$NR^1R^2$, or
h) —O$SO_2R^3$; and $R^{29a}$ and $R^{29b}$ are independently:
a) —H,
b) =O,
c) —($CH_2$)$_s$—O[(C=O)O$_r$]$_s$$C_1$–$C_{10}$-alkyl, alkyl as defined above,
d) —($CH_2$)$_s$—O[(C=O)O$_r$]$_s$$C_2$–$C_{10}$-alkenyl, alkenyl as defined above,
e) —($CH_2$)$_s$—O[(C=O)O$_r$]$_s$$C_2$–$C_6$-alkynyl, alkynyl as defined above,
f) —($CH_2$)$_s$—O[(C=O)O$_r$]$_s$($C_3$–$C_7$)-cycloalkyl,
g) —($CH_2$)$_s$—O[(C=O)O$_r$]$_s$aryl, aryl as defined above, h) —$(CH_2)_s$—$O[(C=O)O_r]_s$heteroaryl, heteroaryl as defined above, i) —$(CH_2)_s$—$O(CH_2)_nO(CH_2)_m$heteroaryl, heteroaryl as defined above, j) —$(CH_2)_s$—$O(CH_2)_nO(CH_2)_m$aryl, aryl as defined above, k) —$(CH_2)_s$—$OC(=O)NR^1R^2$, l) —$(CH_2)_s$—$OSO_2R^3$, m) —$(C_1$–$C_6)$-alkyl, alkyl as defined above, n) —$(C_2$–$C_6)$-alkenyl, alkenyl as defined above, or o) =$C(C_1$–$C_{10}$-alkyl)$_2$, alkyl as defined above.

An embodiment of this embodiment are the compounds of structural Formula I or a pharmaceutically acceptable salt, crystal form or hydrate, wherein:

$R^4$ is:

a) —$O[(C=O)O_r]_s$aryl, wherein aryl is defined as phenyl or naphthyl, unsubstituted or substituted with one, two or three substituents selected from the group consisting of: Br, Cl, F, I, $(C_1$–$C_6)$-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, or b) —$O[(C=O)O_r]_s$heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1$–$C_6)$-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

An embodiment of the invention are the compounds of Formula I

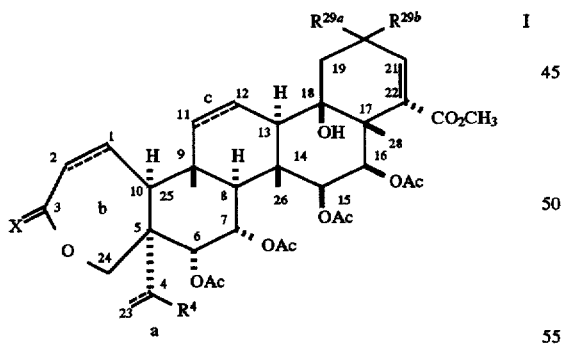

or a pharmaceutically acceptable salt, crystal form, or hydrate, wherein:

X is: H, $R^1$;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:

a) H, or b) $(C_1$–$C_6)$-alkyl, wherein alkyl is unsubstituted or substituted with one, two or three substituents selected from the group consisting of: Br, Cl, F, I, $(C_1$–$C_6)$-alkoxy, vinyl, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl, wherein aryl is defined as phenyl or naphthyl, unsubstituted or substituted with one, two or three substituents selected from the group consisting of: Br, Cl, F, I, $(C_1$–$C_6)$-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1$–$C_6)$-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:

a) —$(C_1$–$C_6)$-alkyl, alkyl as defined above;

b) —$(C_1$–$C_6)$-alkenyl, wherein alkenyl is unsubstituted or substituted with one, two or three substituents selected from the group consisting of: Br, Cl, F, I, $(C_1$–$C_6)$-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above;

c) —$(C_1$–$C_6)$-alkynyl, wherein alkynyl is unsubstituted or substituted with one, two or three substituents selected from the group consisting of: Br, Cl, F, I, $(C_1$–$C_6)$-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above, d) -aryl, aryl as defined above, or e) -heteroaryl, heteroaryl as defined above;

$R^4$ is:

a) absent and a is a double bond;

b) —H, c) —OH, d) =O, e) —$O[(C=O)O_r]_sC_1$–$C_{10}$-alkyl, alkyl as defined above, f) —$O[(C=O)O_r]_sC_2$–$C_{10}$-alkenyl, as defined above, g) —$O[(C=O)O_r]_sC_2$–$C_6$-alkynyl, alkynyl as defined above, h) —$O[(C=O)O_r]_s(C_3$–$C_7)$-cycloalkyl, i) —$O[(C=O)O_r]_s$aryl, aryl as defined above, j) —$OC(=O)O[(C=O)O_r]_s$heteroaryl, heteroaryl as defined above, k) —$O(CH_2)_nO(CH_2)_m$heteroaryl, heteroaryl as defined above, l) —$O(CH_2)_nO(CH_2)_m$aryl, aryl as defined above, m) —$OC(=O)NR^1R^2$, n) —$OSO_2R^3$, or o) —$NR^1R^2$; and $R^{29a}$ and $R^{29b}$ are independently:
a) —H,
b) =O,
c) —(CH$_2$)$_s$—O[(C=O)O$_r$]$_s$C$_1$–C$_{10}$-alkyl, alkyl as defined above,
d) —(CH$_2$)$_s$—O[(C=O)O$_r$]$_s$C$_2$–C$_{10}$-alkenyl, alkenyl as defined above,
e) —(CH$_2$)$_s$—O[(C=O)O$_r$]$_s$C$_2$–C$_6$-alkynyl, alkynyl as defined above,
f) —(CH$_2$)$_s$—O[(C=O)O$_r$]$_s$(C$_3$–C$_7$)-cycloalkyl,
g) —(CH$_2$)$_s$—O[(C=O)O$_r$]$_s$aryl, aryl as defined above,
h) —(CH$_2$)$_s$—O[(C=O)O$_r$]$_s$heteroaryl, heteroaryl as defined above,
i) —(CH$_2$)$_s$—O(CH$_2$)$_n$O(CH$_2$)$_m$heteroaryl, heteroaryl as defined above,
j) —(CH$_2$)$_s$—O(CH$_2$)$_n$O(CH$_2$)$_m$aryl, aryl as defined above,
k) —(CH$_2$)$_s$—OC(=O)NR$^1$R$^2$,
l) —(CH$_2$)$_s$—OSO$_2$R$^3$,
m) —(C$_1$–C$_6$)-alkyl, alkyl as defined above,
n) —(C$_2$–C$_6$)-alkenyl, alkenyl as defined above, or
o) =C(C$_1$–C$_{10}$-alkyl)$_2$, alkyl as defined above.

An embodiment of this embodiment of the invention are the compounds of Formula I

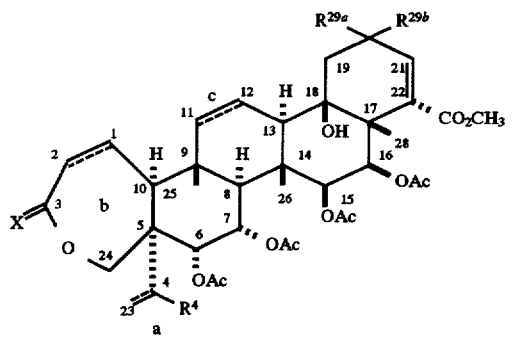

or a pharmaceutically acceptable salt, crystal form, or hydrate, wherein:
X is: H, R$^1$;
a is: a single bond;
b is: a single bond or a double bond;
n is: 1 to 4;
m is: 1 to 4;
r is: 0 or 1;
s is: 0 or 1;
R$^1$ and R$^2$ are independently:
a) H, or
b) (C$_1$–C$_6$)-alkyl, wherein alkyl is unsubstituted or substituted with one, two or three substituents selected from the group consisting of: Br, Cl, F, I, (C$_1$–C$_6$)-alkoxy, vinyl, cyano, oxo, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, aryl, wherein aryl is defined as phenyl or naphthyl, unsubstituted or substituted with one, two or three substituents selected from the group consisting of: Br, Cl, F, I, (C$_1$–C$_6$)-alkoxy, phenyl, phenoxy, cyano, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, (C$_1$–C$_6$)-alkoxy, cyano, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

R$^3$ is:
a) —(C$_1$–C$_6$)-alkyl, alkyl as defined above;
b) —(C$_1$–C$_6$)-alkenyl, wherein alkenyl is unsubstituted or substituted with one, two or three substituents selected from the group consisting of: Br, Cl, F, I, (C$_1$–C$_6$)-alkoxy, cyano, oxo, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, aryl as defined above, and heteroaryl as defined above;
c) —(C$_1$–C$_6$)-alkynyl, wherein alkynyl is unsubstituted or substituted with one, two or three substituents selected from the group consisting of: Br, Cl, F, I, (C$_1$–C$_6$)-alkoxy, cyano, oxo, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, aryl as defined above, and heteroaryl as defined above,
d) -aryl, aryl as defined above, or
e) -heteroaryl, heteroaryl as defined above;

R$^4$ is:
a) —OH,
b) —O[(C=O)O$_r$]$_s$C$_1$–C$_{10}$-alkyl, alkyl as defined above,
c) —O[(C=O)O$_r$]$_s$(C$_3$–C$_7$)-cycloalkyl,
d) —O[(C=O)O$_r$]$_s$aryl, aryl as defined above,
e) —O[(C=O)O$_r$]$_s$heteroaryl, heteroaryl as defined above,
f) —O(CH$_2$)$_n$O(CH$_2$)$_m$heteroaryl, heteroaryl as defined above,
g) —O(CH$_2$)$_n$O(CH$_2$)$_m$aryl, aryl as defined above,
h) —OC(=O)NR$^1$R$^2$, or
i) —OSO$_2$R$^3$;

$R^{29a}$ and $R^{29b}$ are independently:
a) —H,
b) =O,
c) —(CH$_2$)$_s$—O[(C=O)O$_r$]$_s$C$_1$–C$_{10}$-alkyl, alkyl as defined above,
d) —(CH$_2$)$_s$—O[(C=O)O$_r$]$_s$C$_2$–C$_{10}$-alkenyl, alkenyl as defined above,
e) —(CH$_2$)$_s$—O[(C=O)O$_r$]$_s$C$_2$–C$_6$-alkynyl, alkynyl as defined above,
f) —(CH$_2$)$_s$—O[(C=O)O$_r$]$_s$(C$_3$–C$_7$)-cycloalkyl,
g) —(CH$_2$)$_s$—O[(C=O)O$_r$]$_s$aryl, aryl as defined above,
h) —(CH$_2$)$_s$—O[(C=O)O$_r$]$_s$heteroaryl, heteroaryl as defined above,
i) —(CH$_2$)$_s$—O(CH$_2$)$_n$O(CH$_2$)$_m$heteroaryl, heteroaryl as defined above,
j) —(CH$_2$)$_s$—O(CH$_2$)$_n$O(CH$_2$)$_m$aryl, aryl as defined above,
k) —(CH$_2$)$_s$—OC(=O)NR$^1$R$^2$,
l) —(CH$_2$)$_s$—OSO$_2$R$^3$,
m) —(C$_1$–C$_6$)-alkyl, alkyl as defined above,
n) (C$_2$–C$_6$)-alkenyl, alkenyl as defined above, or
o) =C(C$_1$–C$_{10}$-alkyl)$_2$, alkyl as defined above.

An embodiment of the invention is a compound selected from the group consisting of:

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-en-3-one;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-1,21-dien-3-one;

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-ene;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-1,21-diene;

4,6,7,15,16-pentakis(acetyloxy)-18-hydroxy-22-methoxycarbonyl[6α,7α,15β,16β]D:A-Friedo-A-homo-27,30-dinor-24-oxaoleana-1,20(29),21-trien-3-one;

4,6,7,15,16-pentakis(acetyloxy)-18-hydroxy-22-methoxycarbonyl[6α,7α,15β,16β]D:A-Friedo-A-homo-27,30-dinor-24-oxaoleana-1,21-dien-3,20-dione;

4-(2-bromobenzoyl)oxy-6,7,15,16-tetrakis(acetyloxy)-18-hydroxy-22-methoxycarbonyl[6α,7α,15β,16β,20α]:A-Friedo-A-homo-27,30-dinor-24-oxaoleana-1,21-dien-3-one;

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-21-en-3-one;

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaolean;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-21-ene;

4,6,7,15,16-pentakis(acetyloxy)-18-hydroxy-22-methoxycarbonyl[6α,7α,15β,16β]D:A-Friedo-A-homo-27,30-dinor-24-oxaoleana-20(29),21-dien-3-one 4,6,7,15,16-pentakis(acetyloxy)-18-hydroxy-22-methoxycarbonyl[6α,7α,15β,16β]D:A-Friedo-A-homo-27,30-dinor-24-oxaoleana-21-en-3,20-dione;

4-(2-bromobenzoyl)oxy-6,7,15,16-tetrakis(acetyloxy)-18-hydroxy-22-methoxycarbonyl[6α,7α,15β,16β,20α]D:A-Friedo-A-homo-27,30-dinor-24-oxaoleana-21-en-3-one;

4-(2-bromobenzoyl)oxy-6,7,15,16-tetrakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. "Halogen", as used herein, means fluoro, chloro, bromo and iodo.

The term "aryl" is defined as a phenyl or naphthyl ring which is optionally substituted at any available carbon atoms with one, two or three substituents selected from the group consisting of: Br, Cl, F, I, ($C_1$–$C_6$)-alkoxy, phenyl, phenoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein is intended to include the following a 5 or 6-membered ring substituted with one or two heteroatoms selected from O, S, N, and is unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens selected from the, the remaining ring atoms being carbon, selected from the group consisting of: dioxolanyl, dihydrofuranyl, dihydropyranyl, and dioxanyl.

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. As will be understood by those skilled in the an, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

REACTION SCHEME A

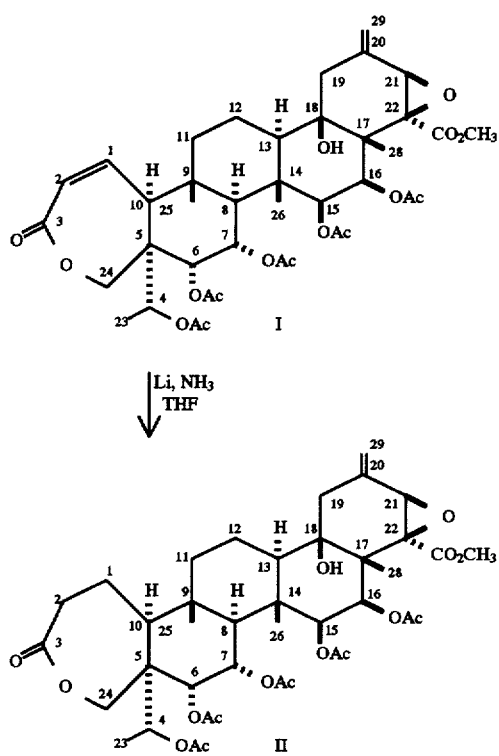

As seen in Scheme A, compound I, 4,5,6,15,16-pentakis (acetyloxy)-21,22-epoxy-18-hydroxy-22-methoxycarbonyl [6α,7α,15β,16β,21β,22β]D:A-Freido-A-homo-27,30-dinor-24-oxaoleana-1,20(29)-diene-3-one, isolated from *Spachea correa* in liquid ammonia with lithium metal will result in the reduction of the C1 olefin group to produce the saturated lactone. Alternative methods for reducing the C1 olefin group and/or the C20(29) olefin that are known in the art may also be employed. U.S. Ser. No. 08/476,806 filed on Jun. 7, 1995 describes the isolation of compound I and is hereby incorporated by reference. The resultant lactone can then be converted to the oxepin analog by procedures described in Reaction Scheme B.

It should also be noted that compounds of Formula I having the 11,12-double bond can be prepared using the starting material, 4,6,7,15,16-pentakisacetoxy-21,22-epoxy-18-hydroxy-22-methoxycarbonyl[6α,7α,15β,16β,21β,22β] D:A-Freido-A-homo-27,30-dinor-24-oxaleana-1,11,20(29)-trien-3-one, isolated from *Spachea correa* and following the procedures described herein. However, there may be reactions where it will not be possible to selectively operate on one of the double bonds, for example, ozonolysis.

REACTION SCHEME B

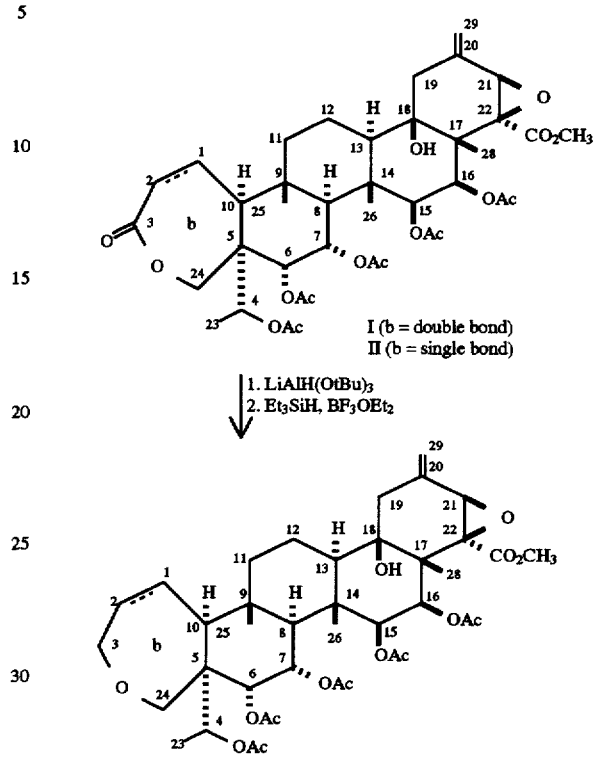

As seen in Scheme B, compound I [(4,6,7,15,16-pentakis (acetyloxy)-21,22-epoxy-18-hydroxy-22-methoxycarbonyl[6α,7α,15β,16β,21β,22β]D:A-Freido-A-homo-27,30-dinor-24-oxaoleana-1,20(29)-dien-3-one], isolated from *Spachea correa* can be converted to its oxepin analog in a two step process. U.S. Ser. No. 08/476,806 filed on Jun. 7, 1995 describing the isolation of compound I and is hereby incorporated by reference. Lactone I is first reduced to the lactol. This can be accomplished by using a variety of reducing agents including di-isobutylaluminum hydride (DIBAL-H) and sodium bis(2-methoxyethoxy) aluminum hydride (Red-Al). A more optimal reducing agent is the use of lithium tri-t-butoxyaluminum hydride in an inert solvent such as dichloromethane at reduced temperatures, preferably 0° C. The purified lactol intermediate is then reacted with triethylsilane and a Lewis acid such as borontrifluoride diethyl etherate to give the ether (oxepin) analog of I.

REACTION SCHEME C

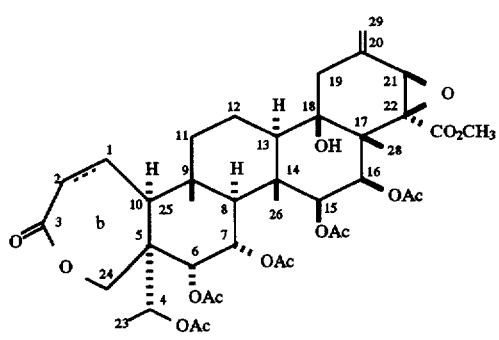

1. LiAlH(OtBu)₃
2. Et₃Al

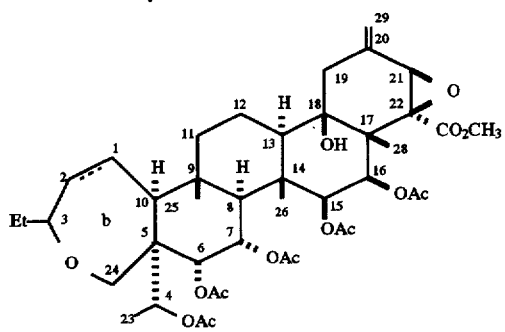

In a variation of Scheme B, oxepin derivatives substituted at C3 can also be prepared. Thus in Reaction Scheme C lactone I is first reduced to the lactol as described in Reaction Scheme B. The purified lactol intermediate is then reacted with a trialkylaluminum reagent, as exemplified in this scheme by triethylaluminum (Et₃Al) to give the ethyl derivative. The allyl derivative can be prepared with allyltrimethylsilane and a Lewis acid such as borontrifluoride diethyl etherate.

REACTION SCHEME D

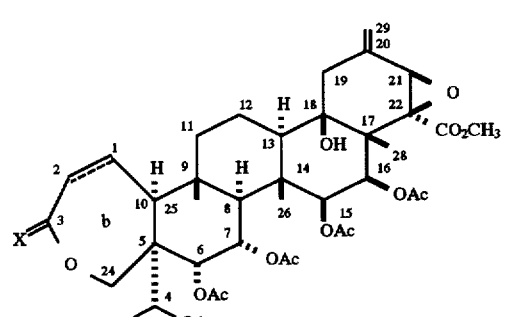

WCl₆, nBuLi
THF, 50° C.

-continued
REACTION SCHEME D

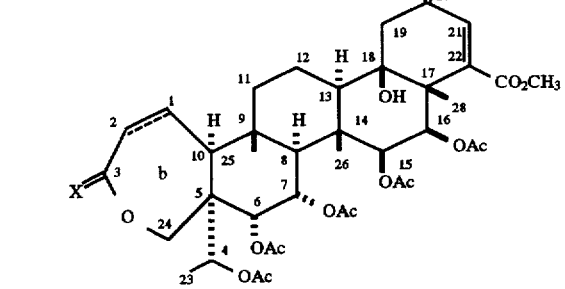

The C21–C22 epoxide of lactone or ether derivatives can be converted to the olefin by use of a WCl₆/BuLi complex (1:2) in tetrahydrofuran (THF) by procedures developed by Sharpless et al. (*J. Am. Chem. Soc.*, 94, 6538–6540, 1972). This conversion can be achieved before or after any of the reaction schemes described.

REACTION SCHEME E

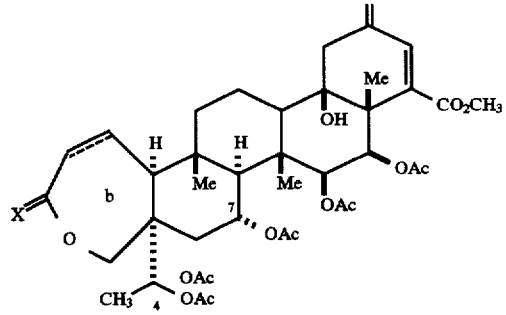

HCl/THF
or
CH₃(Cl)Al[N(OCH₃)CH₃]

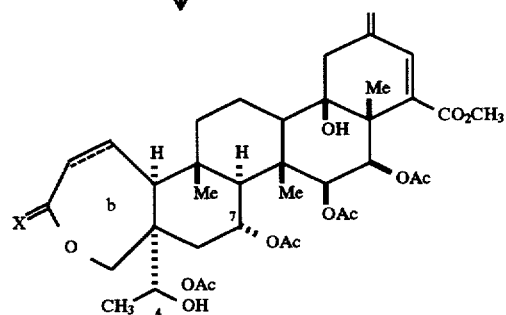

Lactone or ether derivatives can be selectively de-acetylated at C4 to give the corresponding alcohol by reacting it with an aqueous solution of HCl (preferably 2M to 3M concentration) in THF. It can also be prepared by reacting I with CH₃(Cl)Al[N(OCH₃)CH₃] (Weinreb reagent) in inert solvents such as THF, toluene or methylene chloride.

If a product from this reaction contains the epoxide, it can be removed by the method described in Reaction Scheme D.

REACTION SCHEME F

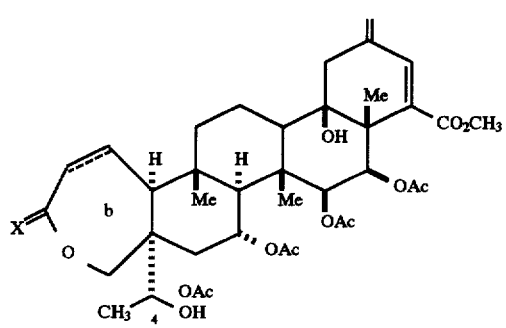

↓ [O]

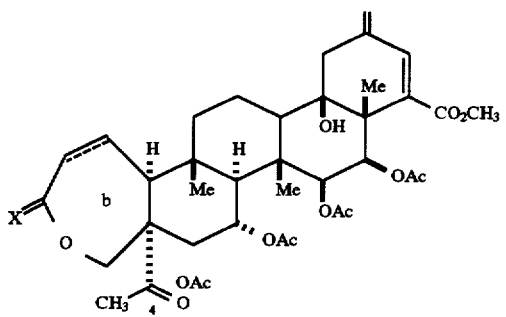

The C4 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

REACTION SCHEME G

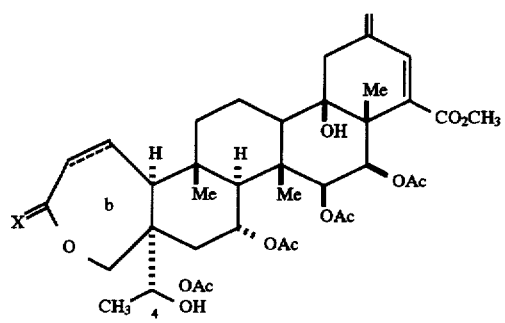

↓ (PhO)$_3$MePI
  HMPT, 75° C.

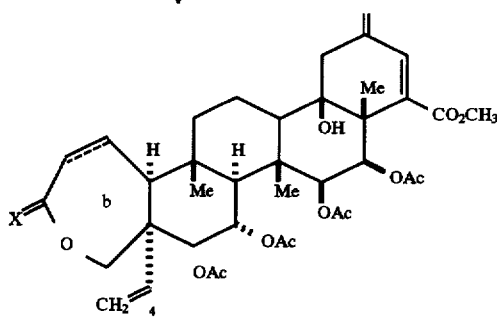

The C4 hydroxy group can be dehydrated to give the olefin. Reaction of the alcohol with tris-phenoxymethylphosphonium iodide in hexamethylphosphorous triamide (HMPT) at 75° C. will achieve this conversion.

REACTION SCHEME H

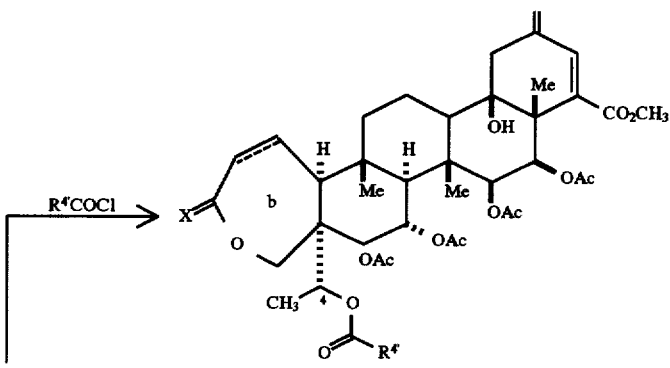

-continued
REACTION SCHEME H
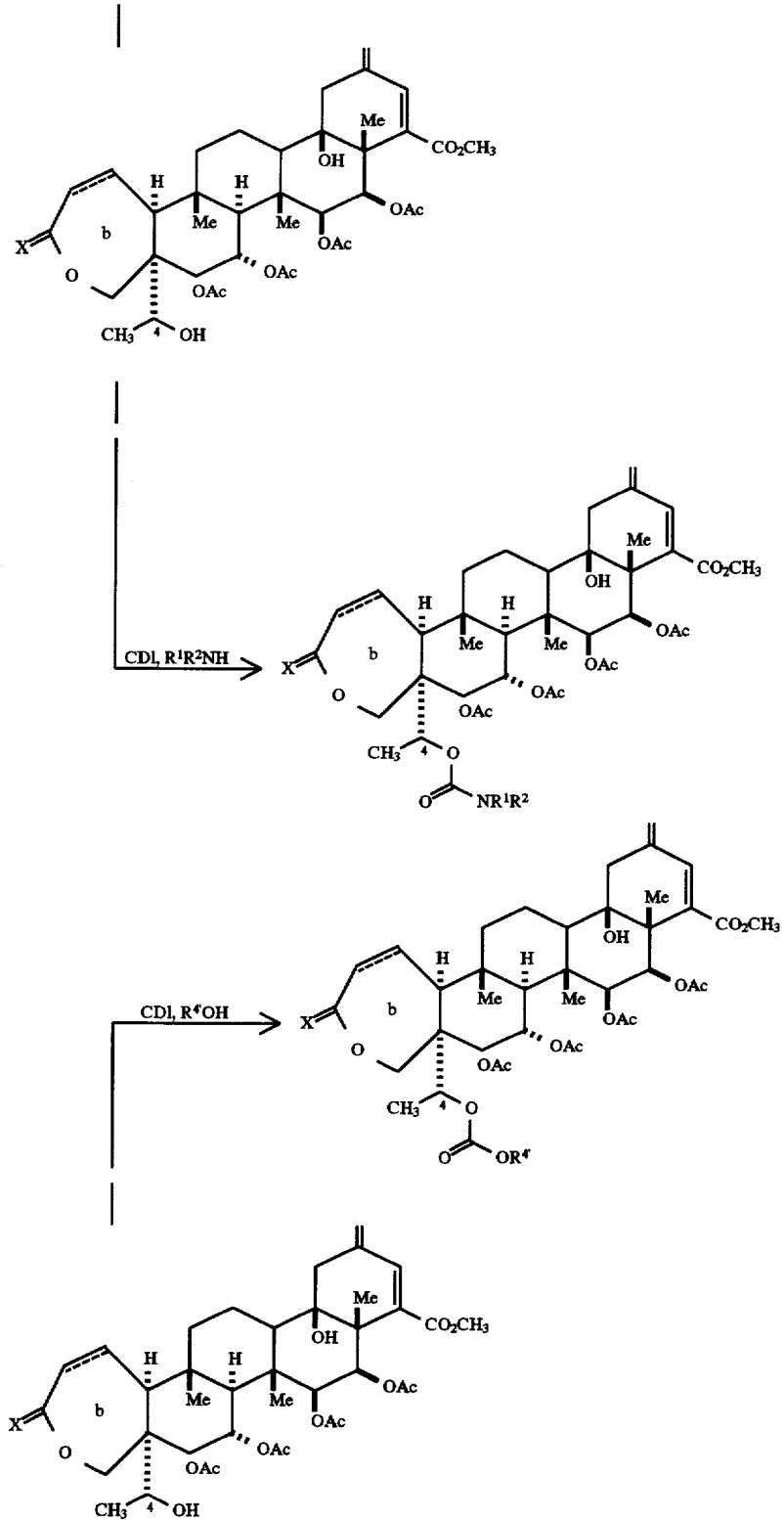

-continued
REACTION SCHEME H

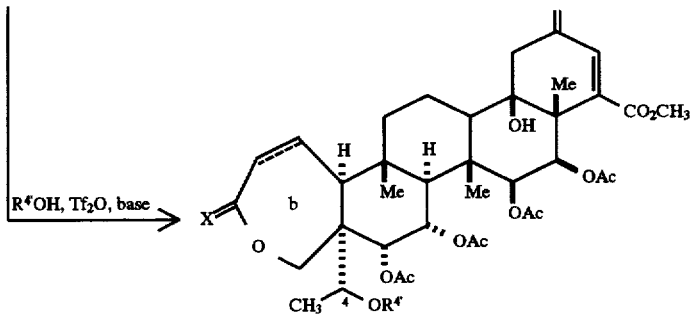

As depicted in Reaction Scheme H, esters at C4 can be prepared by reaction of a preformed carboxylic acid chloride with the C4 alcohol derivative (Reaction Scheme E) in a basic solvent such as pyridine. It should be understood that $R^{4'}$ is used to represent a portion of the $R^4$ definition, e.g. $R^4$ can be an alkyl carbonate which is depicted in the scheme as $OC(=O)OR^{4'}$, $R^{4'}$ representing the alkyl substituent. The acid chlorides, when not purchased, are prepared by stirring the carboxylic acids in reagents such as oxalyl chloride or thionyl chloride. Esters may also be prepared by reaction of the acid chloride and C4 alcohol with silver cyanide (AgCN) in an aprotic solvent such as HMPA. C4 sulfonate derivatives are prepared in a similar manner by reaction with sulfonyl chlorides.

C4 carbonate and carbamate derivatives are prepared by first reacting the C4 alcohol derivative with carbonyldiimidazole (CDI) to obtain the imidazolecarbonyl intermediate which is then reacted with an alcohol or amine ($R^1R^2NH$) to give the corresponding carbonate or carbamate derivatives.

C4 ether derivatives can also be prepared. The best procedure involves reacting an alcohol with trifluoromethanesulfonic anhydride ($Tf_2O$, triflic anhydride) to obtain the preformed triflate in dichloromethane at reduced temperature, preferably $-78°$ C. To this solution is added the triterpene alcohol, the reaction mixture is warmed to room temperature and stirring is continued until reaction is complete. Ethers may also be prepared by heating a mixture of triterpene C4 alcohol, the appropriate alkylhalide and an excess of silver oxide ($Ag_2O$) in an aprotic invert solvent such as THF.

REACTION SCHEME I

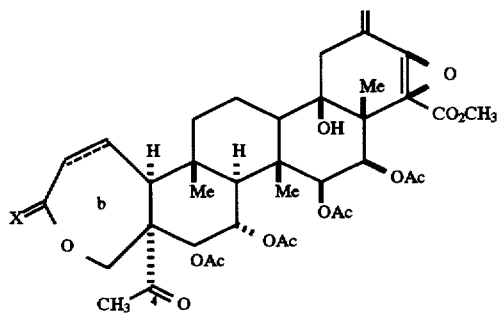

-continued
REACTION SCHEME I

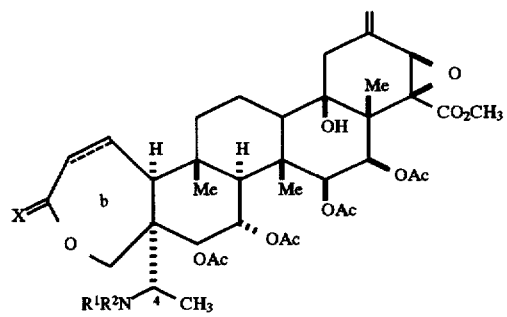

Amines at C4 can be prepared from the C4 ketone described in Reaction Scheme F by reaction with an amine $R^1R^2NH$ in a variety of solvents with a reducing agent such as sodium cyanoborohydride.

REACTION SCHEME J

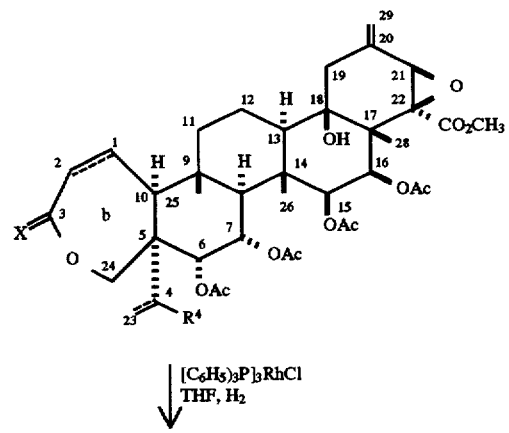

REACTION SCHEME J
-continued

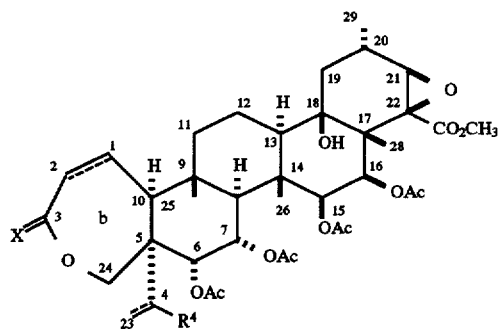

WCl₆, nBuLi
THF, 50° C.

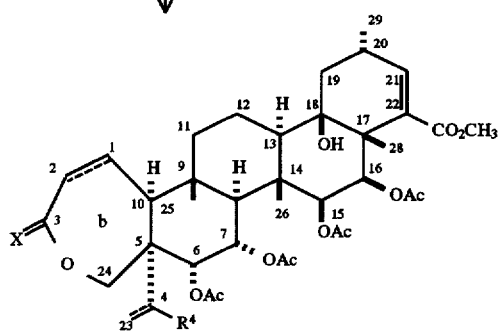

Lactone or ether (oxepin) derivatives which have or have not been derivatized at C4 can be selectively hydrogenated at the C20 position to give the methyl analog. This conversion can be achieved by hydrogenation with tris(triphenylphosphine)rhodium(I)chloride (Wilkinson's catalyst) in THF at 15 to 80 psi for several days.

The C21–C22 epoxide of lactone or ether derivatives can then be converted to the olefin by use of a WCl₆/BuLi complex (1:2) in tetrahydrofuran (THF) by procedures described in reaction scheme D.

REACTION SCHEME K

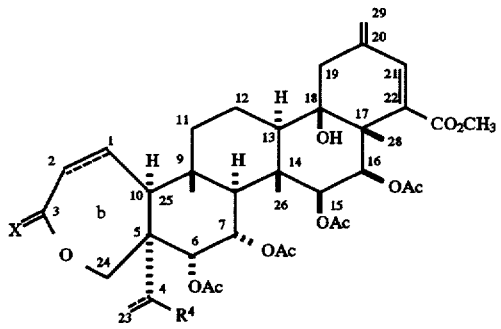

[C₆H₅)₃P]₃RhCl
THF, H₂

REACTION SCHEME K
-continued

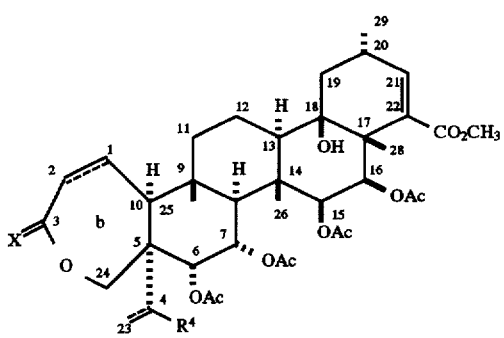

In an alternative to Reaction Scheme J, diene lactone or ether (oxepin) derivatives (Reaction Scheme D) which have or have not been derivatized at C4 can be selectively hydrogenated at the C20 position to give the methyl analog. This conversion can be achieved by hydrogenation with Tris(triphenylphosphine)rhodium(I)chloride (Wilkinson's catalyst) in THF at 15 to 80 psi for several days.

REACTION SCHEME L

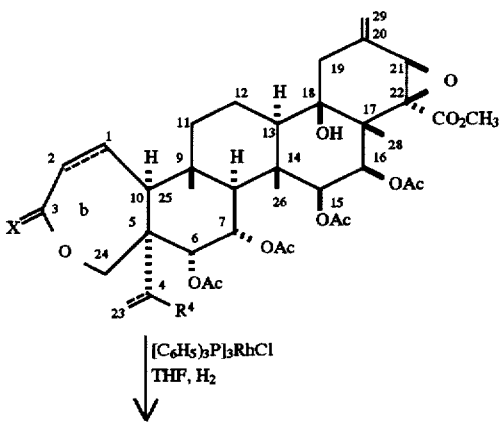

[C₆H₅)₃P]₃RhCl
THF, H₂

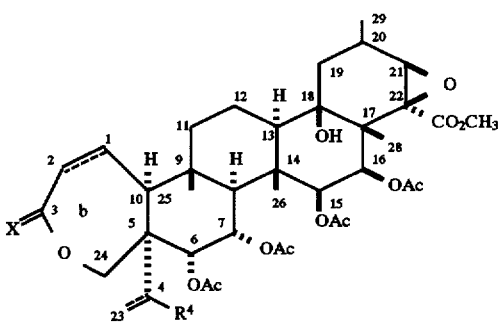

WCl₆, nBuLi
THF, 50° C.

-continued
REACTION SCHEME L

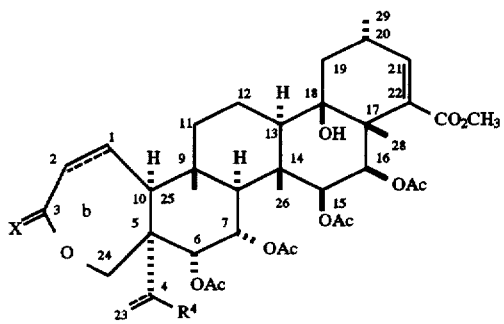

The C20–29 olefin can be selectively converted to the corresponding ketone by a variety of oxidative cleavage procedures. Ozonization ($O_3$) at reduced temperatures, preferrably at −78° C. in dichloromethane and methanol gives the ketone in good yield. Alternatively, the C20 ketone can be prepared by sequential reaction with osmium tetroxide or ruthenium tetroxide and sodium periodate.

The epoxide can then be removed by procedures described in reaction scheme D.

REACTION SCHEME M

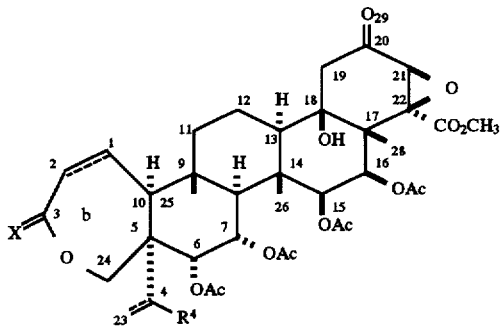

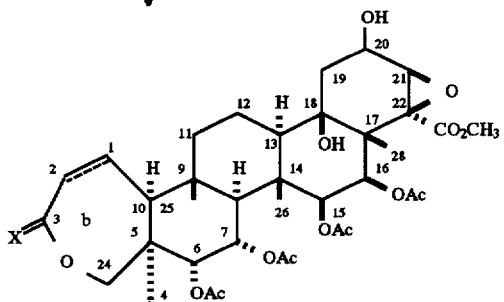

-continued
REACTION SCHEME M

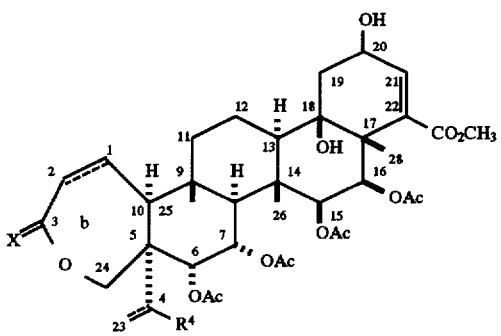

The C20 ketone can be reduced to its corresponding alcohol by using a variety of reducing agents. In particular, tetramethylammonium triacetoxyborohydride in THF is effective. The epoxide can then be removed by procedures described in reaction scheme D.

REACTION SCHEME N

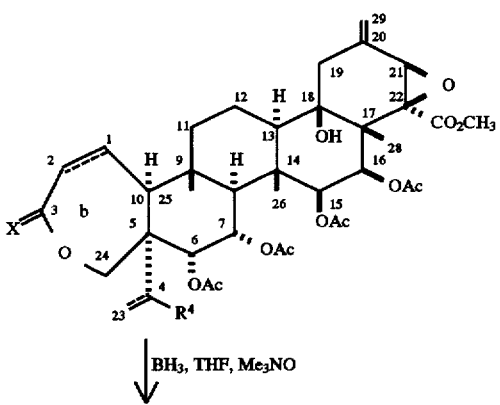

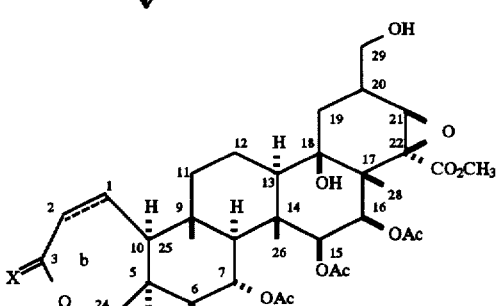

29
-continued
REACTION SCHEME N

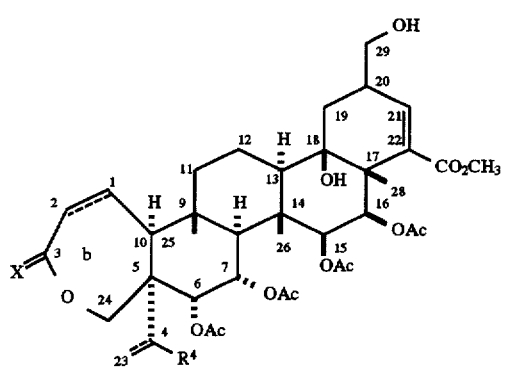

The C20–29 olefin can be converted to the C20 hydroxymethyl derivative. One procedure involves reaction with diborane in THF followed by oxidative workup with trimethylamine-N-oxide (Me$_3$NO).

The epoxide is then removed by procedures described in reaction scheme D.

REACTION SCHEME O

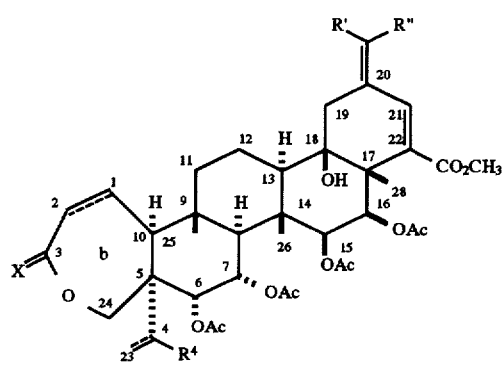

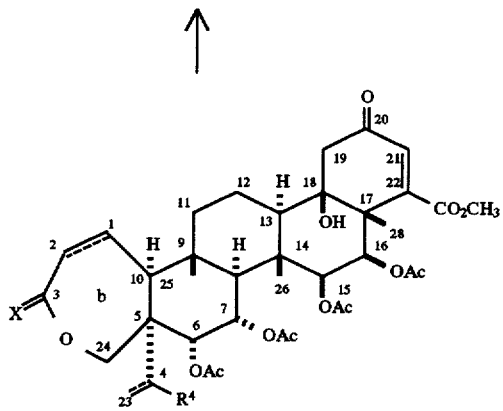

30
-continued
REACTION SCHEME O

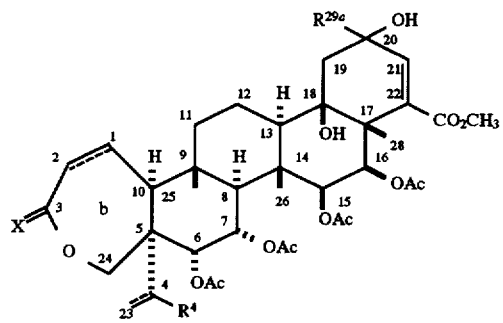

The C20 ketone derivative can be reacted to produce olefins with a variety of well known olefination agents. A particularly useful reagent is the Horner-Emmons-type of olefination reagent [(RO)$_2$P(O)CR'R"]. This produces a mixture of geometric isomers.

Alternatively, the C20 ketone can be reacted with nucleophiles (R$^{29a'}$−M$^+$) to give C20 substituted hydroxy derivatives. In general, Grignard reagents (R$^{29a'}$MgBr) or alkyllithium reagents (R$^{29a'}$Li) are utilized in aprotic solvents such as diethyl ether or THF.

It should be understood that R', R", R$^{29a'}$ and R$^{29b'}$ are used to represent a portion of the R$^{29a}$ and R$^{29b}$ definitions, e.g. R$^{29a}$ can be a substituted olefin which is depicted in the scheme as =CR'R", R' and R" representing alkyl substituents.

REACTION SCHEME P

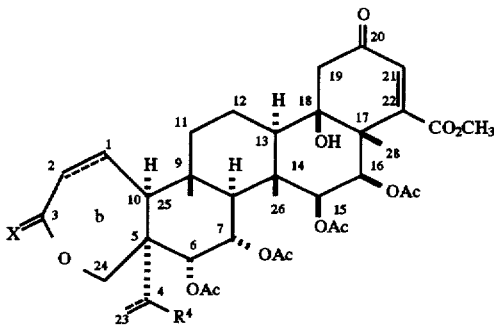

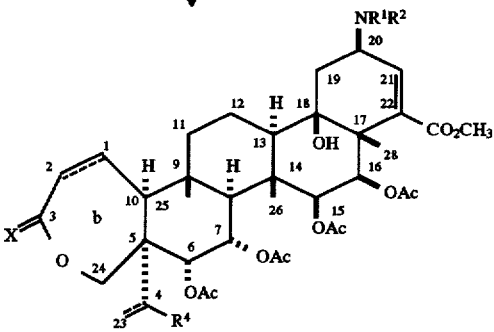

Amines at C20 can be prepared from the C20 ketone by reaction with an amine R$^1$R$^2$NH in a variety of solvents with a reducing agent such as sodium cyanoborohydride.

REACTION SCHEME Q

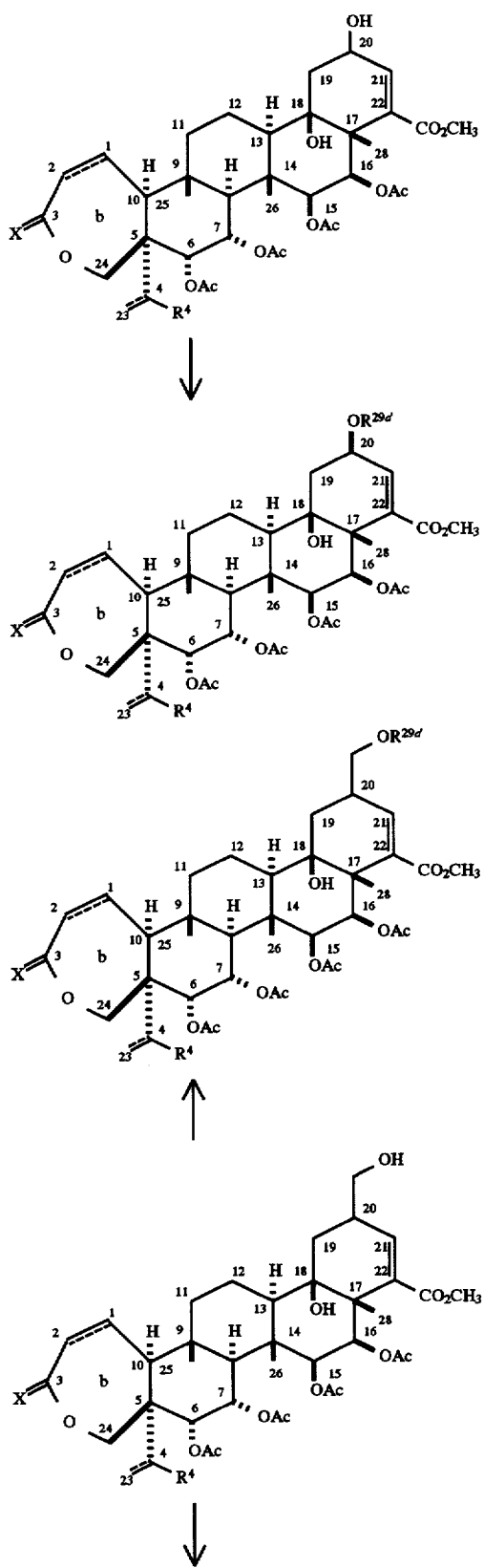

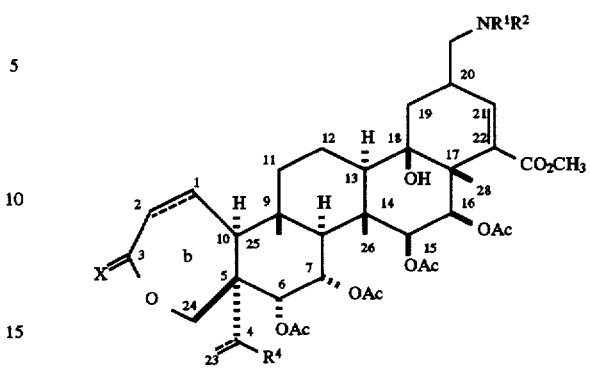

The C20 hydroxy derivative (Reaction Scheme M) or the C20 hydroxymethyl derivative (Reaction Scheme N) can be converted to ether, ester, carbonate, carbamate, sulfonate and other related derivatives by procedures commonly practiced in the art and as described in Reaction Scheme H.

The C20 hydroxymethyl derivative may also be derivatized as a methanesulfinate ester or triflate ester by standard procedures. The methansulfinate or triflate can then be reacted with an amine $NR^1R^2H$ to give amine derivatives.

UTILITY

The present invention is related to compounds of formula I, including but not limited to those specified in the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hypenhyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation, or ischemic disease (for example, thrombosis and cardiac infarction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta siderosis retinitis, pigmentosa senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

A method of treating a condition in a mammal, the treatment of which is effected or facilitated by $K_v1.3$ inhibition, comprising the administration, in an amount that is effective at inhibiting $K_v1.3$, of a compound of Formula L The method of treating a condition in a mammal, the treatment of which is effected or facilitated by $K_v1.3$ inhibition, wherein the condition is selected from the group consisting of: immunemediated diseases such as the resistance by transplantation of organs or tissue such as heart, kidney, liver, medulla ossium, skin, cornea, lung, pancreas, intestinum tenue, limb, muscle, nervus, duodenum, smallbowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern aleopreia or alopecia senilis by preventing epilation or providing hair germination and/or promoting hair generation and hair growth; muscular dystrophy; Pyoderma and Sezary's syndrome; Addison's disease; active oxygenmediated diseases, as for example organ injury such as ischemia-reperfusion injury of organs (such as heart, liver, kidney and digestive tract) which occurs upon preservation, transplantation or ischemic disease (for example, thrombosis and cardiac infarction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lungoxygen or drug (for example, paracort and bleomycins), lung cancer and pulmonary emphysema; ocular diseases such as cataracta, siderosis, retinitis, pigmentosa senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and immunodepression or a disorder involving immunodepression, such as AIDS, cancer, senile dementia, trauma (including wound healing, surgery and shock), chronic bacterial infection, and certain central nervous system disorders.

An embodiment of the invention is a method for the treatment of autoimmune diseases. Another embodiment of the invention is a method for the prevention of rejection of foreign organ transplants comprising administering to a patient in need of such treatment a therapeutically effective amount of a compound of formula I.

One end result of an autoimmune or a rejection process is tissue destruction caused by inflammatory cells and the mediators they release. Anti-inflammatory agents such as NSAID's and corticosteroids act principally by blocking the effect or secretion of these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A, which was approved by the US FDA in 1983, is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting fewer side effects are constantly being searched for in the field. The present invention provides for immunosuppressant agents which are inhibitors of a voltage dependent potassium channel, $K_v1.3$, that is found on human T-lymphocytes.

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of $K^+$ channels, in their role as modulators of the plasma membrane potential in human T-lymphocytes, has been postulated to play a role in eliciting immunosuppressive responses. In regulating membrane potential, $K^+$ channels play a role in the regulation of intracellular $Ca^{++}$ homeostasis, which has been found to be important in T-cell activation. The biochemical characterization of $K^+$ channels is underdeveloped, due to the paucity of selective high affinity probes.

Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

The $K_v1.3$ channel is a voltage-gated potassium channel that is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., Nature, 307, 465, 1984). However, the K+ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci. USA*, 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci. USA*, 89, 10094, 1992). Margatoxin, on the other hand, blocks only $K_v1.3$ in T-cells, and has immunosuppressant activity in both in vitro and in vivo models. (Lin et al., *J. Exp. Med*, 177, 637, 1993). Since the compounds of the embodiments of this invention produce blockade of $K_v1.3$, they will also inhibit T-cell activation.

Also within the scope of this invention is a method of treating a condition in a mammal, the treatment of which is effected or facilitated by $K_v1.3$ inhibition, comprising the administration of a pharmaceutical composition comprising a suitable pharmaceutical carrier and a compound of Formula (I), in an amount that is effective at inhibiting $K_v1.3$.

Also within the scope of this invention is a combination therapy comprising a compound of formula I and one or more immunosuppressant agents. These immunosuppressant agents within the scope of this invention include, but are not limited to, IMUREK® azathioprine sodium, brequinar sodium, SPANIDIN® gusperimus trihydrochloride (also known as deoxyspergualin), mizoribine (also known as bredinin), CELLCEPT® mycophenolate mofetil, NEORAL®. Cyclosporin A (also marketed as different formulation of Cyclosporin A under the trademark SANDIMMUNE®), PROGRAF® tacrolimus (also known as FK-506) and RAPIMMUNE® sirolimus (also known as rapamycin), leflunomide (also known as HWA-486), glucocortcoids, such as prednisolone and its derivatives, antibody therapies such as orthoclone (OKT3) and Zenapax and antithymyocyte globulins, such as thymoglobulins.

Using the methodologies described below, representative compounds of the invention were evaluated and found to exhibit IC50 values of at least <10 µM in any of the assays thereby demonstrating and confirming the utility of the compounds of the invention as $K_v1.3$ inhibitors and immunosuppressants.

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3 \times 10^6$/ml in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 µl/well. The various dilutions of test compound were then added in triplicate wells at 25 µl/well, incubated for 30 min at 37° C. Ionomycin (125 ng/ml), and PMA (1 or 5 ng/ml), were added to the appropriate wells. The culture plates were then incubated at 37° C. in a humidified atmosphere of 5% $CO_2$-95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4–4.5 \times 10^6$ cells/ml in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2× with complete media, these purified T cells were also resuspended at $2–2.5 \times 10^6$ cells/ml in complete media. The various dilutions of the compound were added in triplicates at 50 ul/well of a 96 well flat-bottom microculture plate (Costar, Cambridge, Mass.). T cell suspension was then immediately distributed into the wells at 100 ul/well. After incubating the cells with compound for 30 min. at 37° C. in a humidified atmosphere of 5% $CO_2$-95% air, 20 µl/well of anti-CD3 (Ortho Diagnostic, New Jersey) at final conc. of 0.3 ng/ml was added, followed by 50 µl of the irradiated MNC. The culture plates were then incubated at 37° C. in a humidified atmosphere of 5% $CO_2$-95% air for 72 hours. The proliferation of T lymphocytes was assessed by measurement of tritiated thymidine incorporation. During the last 18–24 hrs. of culturing, the cells were pulse-labeled with 2 µCi/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

KV1.3-RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 µCi/ml, Dupont-NEN) in the glutamine supplemented IMDM. After aspiration of the media, 100 µl of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 µl test samples in Low K Buffer also containing 0.2% BSA and 2 mM ouabain. Samples are tested at either 1 µg/ml for routine screening or at a variety of concentrations encompassing at least 1/10 to 10 times the putative $IC_{50}$ of test compound to determine potency. After a fixed preincubation time, which is usually 10 min. the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 µl are taken from each well after a given time and added to plates containing 100 µl MicroScint-40 (Packard) for counting by liquid scintillation techniques. MicroScint-40 (100 µl) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

DOSAGE FORMS

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE 1

A Method Of Extracting The Compounds Of Formula 1(a) and 1(b) From *Spachea correa*

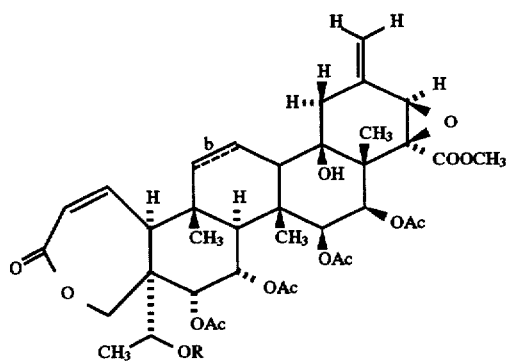

Formula 1(a)b is a single bond and R is OAc
Formula 1(b)b is a double bond and R is OAc One gram of an ethanol extract of the roots of *Spachea correa* was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel 60F$_{254}$ plate of 1 mm thickness using methylene chloride-ethyl acetate 1:1 (v/v) as solvent, then by high performance liquid chromatography (HPLC) using a Zorbax RxC$_8$ 4.6 mm×25 cm column, operated at 50° C. and eluted with a 50 minute gradient of acetonitrile-:water (1:1, v/v) to 100% acetonitrile, delivered at 1 ml/min, to afford 4 mg of compound 1(a) and 1 mg of 1(b).

Homogeneity of the preparations was ascertained in several TLC systems, such as E. Merck silica gel 60F$_{254}$, methylene chloride-ethyl acetate 1:1, Rf 1(a) 0.4, Rf 1(b) 0.3; Whatman KC$_{18}$, methanol-water 9:1, Rf 1(a) 0.65, Rf 1(b) 0.75 and by HPLC using a Zorbax RxC$_8$ column, acetonitrile-water 3:2, k' 1(a) 4.15, k' 1(b) 3.30; and by NMR.

Mass spectra were recorded on JEOL SX-102A (electron impact, EI,903V) and JEOL HX110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature. The FAB spectrum was run in a matrix of dithiothreitol (20/80).

The compound of Formula 1(a) runs underivatized by EI. The molecular ion is observed a m/z 788 and three successive loses of acetic acid are observed. The base peak is observed a m/z 334. The compound does not silylate. Scatming HR-EI indicated a molecular formula of $C_{40}H_{52}O_{16}$. A table of the critical HR-EI data is given below.

| Observed m/z | Formula | Assignment |
|---|---|---|
| 788.3220 | $C_{40}H_{52}O_{16}$ | M+ |
| 728.3040 | $C_{38}H_{48}O_{14}$ | M-acetic acid |
| 668.2834 | $C_{36}H_{44}O_{12}$ | M-2 × acetic acid |
| 334.1417 | $C_{18}H_{22}O_6$ | base peak |

$^{13}$C NMR spectra were recorded for the compound of Formula 1(a) in CD$_2$Cl$_2$ at 100 MHz on a Varian Unity 400 NMR spectrometer at 20° C. Chemical shifts are given in ppm relative to tetramethylsilane (TMS) at zero ppm using the solvent peak at 53.8 ppm as internal standard. The following data were observed: 15.0, 15.2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6, 77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1$H NMR spectra of compound of Formula (a) is provided as FIG. 1. The spectra was recorded at 400 MHz in CD$_2$Cl$_2$ on a Varian Unity 400 NMR spectrometer at 25° C. Chemical shifts are in ppm relative to TMS at zero ppm using the solvent peak at δ5.32 as the internal standard.

The mass spectra of the compound of Formula 1(b) was obtained as above. The following results were obtained.

| Observed m/z | Formula | Assignment |
|---|---|---|
| 786.3075 | $C_{40}H_{50}O_{16}$ | M+ |
| 726.2886 | $C_{38}H_{46}O_{14}$ | M-acetic acid |
| 666.2651 | $C_{36}H_{42}O_{12}$ | M-2 × acetic acid |
| 606.2451 | $C_{34}H_{38}O_{10}$ | M-3 × acetic acid |
| 489.2099 | $C_{26}H_{33}O_9$ | base peak |
| 471.1992 | $C_{26}H_{31}O_8$ | |

$^{13}$C NMR spectra were recorded for the compound of Formula 1(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR EI-MS.

EXAMPLE 2

A Method Of Extracting The Compounds Of Formula 1(c) And 1(d) From *Spachea Correa*

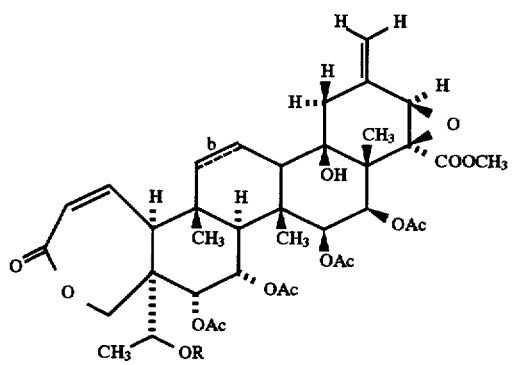

Formula 1(c)b is a single bond and R is OH
Formula 1(d)b is a double bond and R is OH Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride-ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a Zorbax $RxC_8$ 9 mm×25 cm column, maintained at 50° C. and eluted at 4 ml/min with acetonitrile-water 1:1 v/v. Three identical runs finally afforded 100 mg and 20 mg respectively of 1(a) and 1(b) after crystallization from methanol. Later-eluting fractions from the silica gel column above were found to contain at least two related compounds based on UV spectra and color reactions on TLC plates. Material from the methylene chloride-ethyl acetate 1:1 and 1:2 washings were combined and evaporated down. Separation was achieved on the same HPLC column as above, eluting with a 50 minute gradient of 30% to 50% acetonitrile in water. Two identical runs gave 6 mg of purified compound 1(c). Fractions containing the compound of Formula 1(d) were again processed by HPLC (same column) using acetonitrile-water 3:7 delivered isocratically, to yield 2 mg of purified Formula 1(d).

The mass spectra of these compounds were recorded on a Finnigan TSQ700 mass spectrometer (electrospray ionization, ESI). The samples were analyzed by LC/MS using a 2.1×150 mm $C_8$ column at 0.2 ml/min. with a mobile phase of 45% acetonitrile/0.01M aqueous ammonium acetate at 50° C. Component 1(d) had a retention time of 10.5 min. and a molecular weight of 744 which is observed a m/z: 745 (M+H), 762 (M+NH$_3$), 786 (M+H+MeCN). Component 1(c) has a retention time of 11.8 and a molecular weight of 746 which is observed at m/z: 747 (M+H), 764 (M+NH$_3$) and 788 (M+H+MeCN).

The $^{13}C$ NMR spectra obtained for the compound of Formula 1(c) using the conditions previously described is as follows: 15.1 (2×), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2×), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

EXAMPLE 3

Separation By HPLC

Compounds of this invention were characterized by the following behavior during HPLC separation on a Zorbax $RxC_8$ 4.6 mm×25 cm column, maintained at 50° C. and eluted at 1 ml/min with acetonitrile-water 3:2 v/v):

Compound 1(a): k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4

Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4

Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 5

4,6,7,15,16-Pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-en-3-one

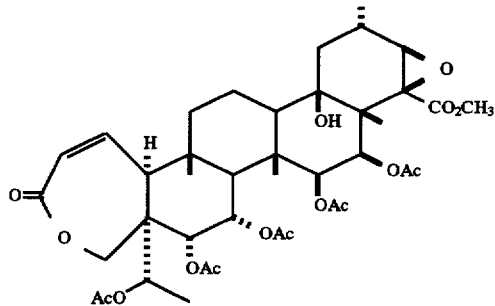

A solution of 50 mg (63.7 μmole) of 4,6,7,15,16-Pentakis(acetyloxy)-21,22-epoxy-18-hydroxy-22-methoxycarbonyl [6α,7α,15β,16β,21β,22β]D:A-Friedo-A-homo-27,30-dinor-24-oxaoleana-1,20(29)-dien-3-one in 50 ml of dry THF was degassed under reduced pressure and saturated with nitrogen, the procedure being repeated several times. 25 mg of Wilkinson's catalyst [(PPh₃)₃RhCl] were added and the solution was degassed and saturated with hydrogen in the previously described manner. The reaction vessel was then pressurized with H₂ to 15 psi (1 atm) and shaken for 65 h at 25° C. After that time the solvent was removed under reduced pressure. The residue was dissolved in a small amount of ethyl acetate/hexanes (2:1) (ca. 1 mL) and filtered through 30 g of silica gel eluting with 500 ml of ethyl acetate/hexanes (2:1). The first fractions, containing the Wilkinson-catalyst (approx. 50 mL) were discarried. The fractions containing the product were combined. After removing the solvent under reduced pressure the crude product was dried in vacuo and purified by HPLC to afford 20.8 mg (42%) of the title compound as a white solid. ¹H NMR (CDCl₃) δ 1.5 (d, 3H, J=8.6 Hz, C29-H), 2.4 (m, 1H, C20-H); Mass Spectrum (APCI): m/e 808.

EXAMPLE 6

4,6,7,15,16-Pentakis(acetyloxy)-18-hydroxy-22-methoxycarbonyl[6α,7α,15β,16β,20α]D:A-Friedo-A-homo-27,30-dinor-24-oxaoleana-1,21-dien-3-one

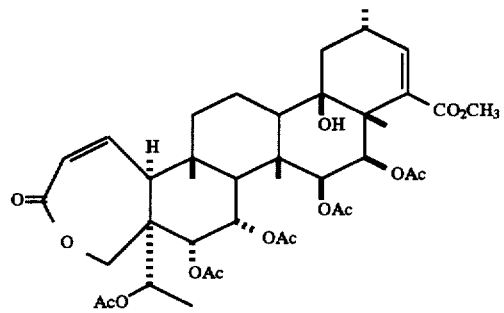

A solution of 48.2 mg (0.104 mmole) of tungsten hexachloride in 8 mL of dry tetrahydrofuran was cooled to −78° C. under nitrogen. Then 0.152 mL (0.208 mmole) of 1.6M butyllithium was added and the solution was allowed to warm to room temperature over 30 min. Then a solution of 20.2 mg (0.026 mmole) of 4,6,7,15,16-Pentakis (acetyloxy)-21,22-epoxy-18-hydroxy-22-methoxycarbonyl [6α,7α,15β,16β,21β,22β]D:A-Friedo-A-homo-27,30-dinor-24-oxaoleana-1-en-3-one in 2 mL of dry tetrahydrofuran was added and the solution was heated under nitrogen at 50° C. for 18 h. The mixture was applied to a 10 cm column of silica gel, which was washed with 2:1 ethyl acetate-hexane. The eluate was concentrated and purified by silica gel chromatography with 2:1 ethyl acetate-hexane to afford 15.9 mg of the title compound as a white solid; Mass Spectrum (APCI) 792 (M+NH₄).

EXAMPLE 7

4,6,7,15,16-Pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-ene

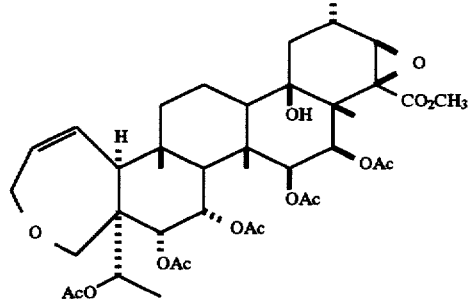

A solution of 213 mg (0.27 mmole) of 4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-en-3-one in 2 mL of dichloromethane was cooled to 0° C. Then 0.68 mL of a 1.02M solution of lithium tri-tertbutoxyaluminum hydride was added and the solution was stirred at 0° C. for 18 h. The reaction was quenched with 10 mL of 2.5M aqueous H₂SO₄ and then was diluted with 50 mL of dichloromethane. After the layers were separated, the organic phase was dried over Na₂SO₄ and concentrated.

The residue was dissolved in a mixture of 5 mL of dichloromethane and 1 mL of triethylsilane. Then 0.8 mL of boron trifluoride-etherate was added and the solution was stirred at room temperature. After 2 h, the reaction was quenched by addition of saturated aqueous $NaHCO_3$ solution and dichloromethane. The layers were separated and the organic layer was washed with and brine, saturated aqueous $NaHCO_3$, dried over $MgSO_4$, and concentrated. The residue was first filtered through a plug of silica gel and then purified by HPLC (Waters RCM, Prep Nova-Pak HR Silica, 25 mm×100 mm) using 8:4:1 hexane:t-butylmethylether:acetonitrile to afford 60.5 mg (29%) of the title compound as a white solid; $^1$H NMR ($CDCl_3$) δ 2.41 (m, 1H, C20-H), 3.38 (s, 1H, C21-H), 3.69 (dd, 2H, AB, J=12 Hz, C24-H), 5.5 (m, 1H, C1-H), 5.57 (m, 1H, C2-H); Mass Spectrum (APCI): m/e 794 (M+$NH_4$).

EXAMPLE 8

4,6,7,15,16-Pentakis(acetyloxy)-18-hydroxy-22-methoxycarbonyl[6α,7α,15β,16β,20α]D:A-Friedo-A-homo-27,30-dinor-24-oxaoleana-1,21-diene

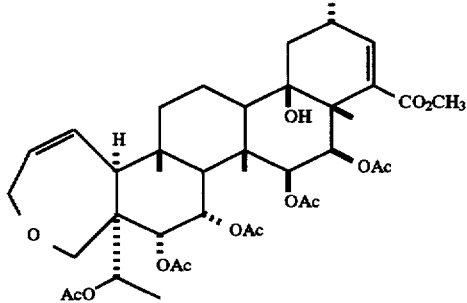

A solution of 233 mg (0.56 mmole) of tungsten hexachloride in 8 mL of dry tetrahydrofuran was cooled to −78° C. under nitrogen. Then 0.70 mL (1.12 mmole) of 1.6M butyl-lithium was added and the solution was allowed to warm to room temperature over 30 min. Then a solution of 111 mg (0.141 mmole) of 4,6,7,15,16-Pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-ene in 2 mL of dry tetrahydrofuran was added and the solution was heated under nitrogen at 50° C. for 18 h. The mixture was applied to a 10 cm column of silica gel, which was washed with 2:1 ethyl acetate-hexane. The eluate was concentrated and purified by silica gel chromatography with 2:1 ethyl acetate-hexane to afford 95 mg (88%) of the title compound as a white solid; $^1$H NMR ($CDCl_3$) δ 2.66 (m, 1H, C20-H), 3.64 and 3.67 (dd, AB, 2H, J=12.2 Hz, C24-H), 6.52 (s, 1H, C21-H); Mass Spectrum (APCI) 778 (M+$NH_4$).

EXAMPLE 9

4,6,7,15,16-pentakis(acetyloxy)-18-hydroxy-22-methoxycarbonyl[6α,7α,15β,16β]D:A-Friedo-A-homo-27,30-dinor-24-oxaoleana-1,20(29),21-trien-3-one

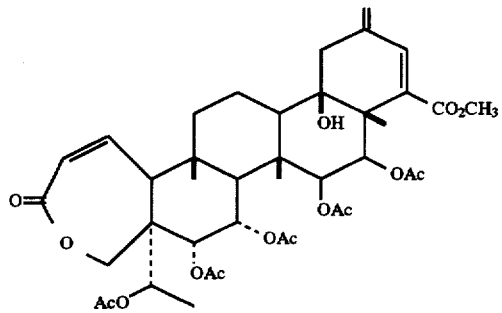

A solution of 233 mg (0.56 mmole) of tungsten hexachloride in 8 mL of dry tetrahydrofuran was cooled to −78° C. under nitrogen. Then 0.70 mL (1.12 mmole) of 1.6M butyl-lithium was added and the solution was allowed to warm to room temperature over 30 min. Then a solution of 111 mg (0.141 mmole) of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one in 2 ml of dry tetrahydrofuran was added and the solution was heated under nitrogen at 55° C. for 14 h. The mixture was applied to a 10 cm column of silica gel, which was washed with 2:1 ethyl acetate-hexane. The eluate was concentrated and purified by silica gel chromatography with 2:1 ethyl acetate-hexane to afford 95 mg (88%) of the title compound as a white solid; $^1$H NMR ($CDCl_3$) δ 7.10 (s, 1H, C21-H); Mass Spectrum (APCI) 790 (M+$NH_4$).

EXAMPLE 10

4,6,7,15,16-pentakis(acetyloxy)-18-hydroxy-22-methoxycarbonyl[6α,7α,15β,16β]D:A-Friedo-A-homo-27,30-dinor-24-oxaoleana-1,21-dien-3,20-dione

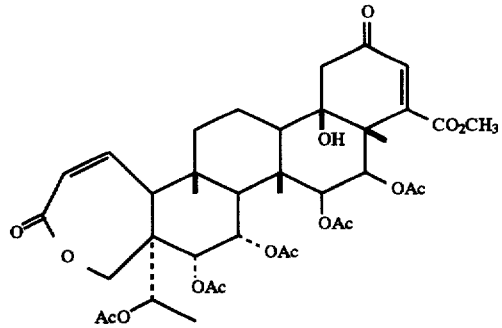

A solution of 120.5 mg of 4,6,7,15,16-pentakis(acetyloxy)-18-hydroxy-22-methoxycarbonyl[6α,7α,15β,16β]D:A-Friedo-A-homo-27,30-dinor-24-oxaoleana-1,20(29),21,22-trien-3-one in 40 ml of ( 1:1, $CH_2Cl_2$/$CH_3OH$) was cooled to −78° C. and $O_3$ was bubbled into the solution until it contained a blue color. The solution was then purged with nitrogen for 3 minutes and 0.3 ml of $Me_2S$ was added. The solution was allowed to warmed to 25° C. for 14 hours.

Volatiles were removed by vaccum and the residue was purified by chromatography on silica gel using 25% ethyl acetate-hexane to afford 100.2 mg of the title compound as a white solid; $^1$H NMR (CDCl$_3$) δ 6.63 (s, 1H), 2.84 (d, 1H, J=17 Hz), 2.74 (d, 1H, J=17 Hz); Mass Spectrum (APCI) m/e 792 (M+NH$_4$).

EXAMPLE 11

4-(2-Bromobenzoyl)oxy-6,7,15,16-Tetrakis (acetyloxy)-18-hydroxy-22-methoxycarbonyl[6α,7α, 15β,16β,20α]D :A-Friedo-A-homo-27,30-dinor-24-oxaoleana-1,21-dien-3-one

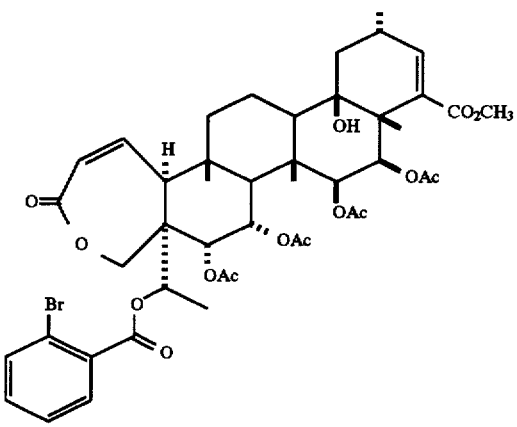

Step A 6,7,15,16-Tetrakis(acetyloxy)-21,22-epoxy-4,18-dihydroxy-22-methoxycarbonyl[6α,7α,15β,16β,21β, 22β]D:A-Friedo-A-homo-27,30-dinor-24-oxaoleana-1,20(29)-dien-3-one

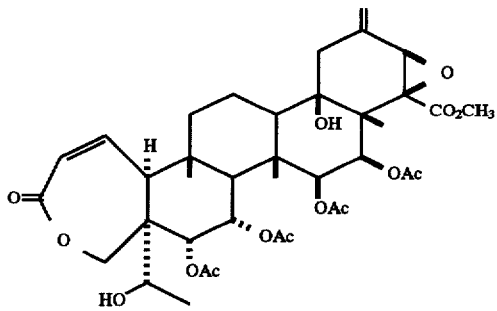

A solution of 102.1 mg (0.130 mmole) of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one in 4 mL of tetrahydrofuran and 2 mL of 3M aqueous HCl was heated at 40° C. for 24 h. The solution was diluted with dichloromethane and the layers were separated. The organic layer was washed with 0.1M phosphate buffer (pH 7), then was dried over MgSO$_4$ and concentrated. The residue was purified by silica gel chromatography with 2:1 ethyl acetate-hexane to afford 44.9 mg of the title compound as a white solid (46%); $^1$H NMR (CDCl$_3$) δ 4.20 (q, 1H, J=4.3 Hz, C4-H); Mass Spectrum (APCI): m/e 764 (M+NH$_4$)

Step B 4-(2-Bromobenzoyloxy)-6,7,15,16-Tetrakis (acetyloxy)-21,22-epoxy-18-hydroxy-22-methoxycarbonyl[6α,7α,15β,16β,21β,22β]D:A-Friedo-A-homo-27,30-dinor-24-oxaoleana-1,20(29)-dien-3-one

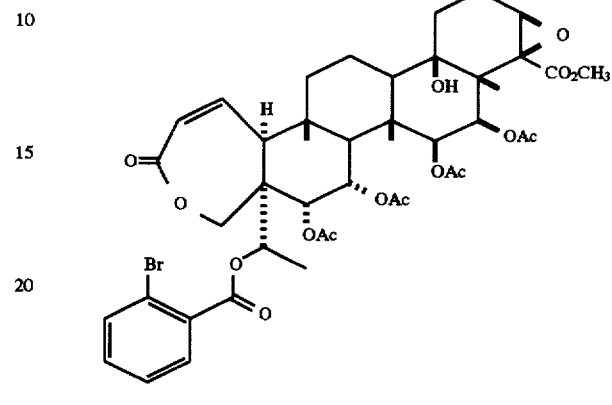

To a solution of 17.5 mg (23.5 µmole) of 6,7,15,16-tetrakis(acetyloxy)-21,22-epoxy-4,18-dihydroxy-22-methoxycarbonyl[6α,7α,15β,16β,21β,22β]D:A -Friedo-A-homo-27,30-dinor-24-oxaoleana-1,20(29)-dien-3-one in 0.5 mL pyridine was added 27.5 mL (237 µmole) of benzoyl chloride. The solution was stirred at room temperature for 4 h, then was concentrated under reduced pressure. The residue was first filtered through a plug of silica gel and then purified by HPLC (Waters RCM, µ Porosil, 10 mm×10 cm) using a mixture of 9.6:6 (5:4:1 hexane-methyl tert-butyl ether-acetonitrile:hexane) to afford 17.3 mg (88%) of the title compound as a white solid; $^1$H NMR δ 5.67 (1H, C4-H), 7.40–7.43 (m, 2H), 7.72 (dd, 1H, J=2.2, 6.9 Hz), 7.78 (dd, 1H, J=2.3, 6.9 Hz); Mass Spectrum (APCI): m/e 946, 948 ($^{79}$Br–M+NH$_4$, $^{81}$Br–M+NH$_4$)

Step C 4-(2-Bromobenzoyl)oxy-6,7,15,16-Tetrakis (acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-en-3-one

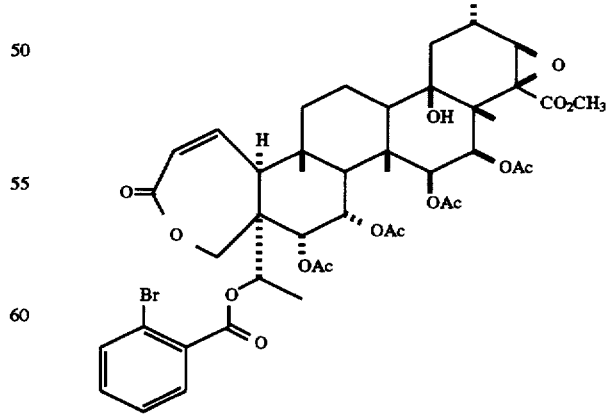

A solution of 0.100 g (0.108 µmole) of 4-(2-bromobenzoyloxy)6,7,15,16-tetrakis(acetyloxy)-21,22- epoxy-18-hydroxy-22-methoxycarbonyl[6α,7α,15β,16β,21β,22β]D:A-Friedo-A-homo-27,30-dinor-24-oxaoleana-1,20(29)-dien-3-one in 20 ml of dry THF was degassed under reduced pressure and saturated with nitrogen, the procedure being repeated several times. Then 75 mg of Wilkinson's catalyst [(PPh₃)₃RhCl] were added and the solution was degassed and saturated with hydrogen in the previously described manner. The reaction vessel was then pressurized with $H_2$ to 50 psi (3.5 atm) and shaken for 72 h at 25° C. After that time the solvent was removed under reduced pressure. The residue was dissolved in a small amount of ethyl acetate/hexanes (1:1) (ca. 1 mL) and filtered through 30 g of silica gel eluting with 500 ml of ethyl acetate/hexanes (1:1). The first fractions, containing the Wilkinson-catalyst (approx. 50 mL) were discarried. The fractions containing the product were combined. After removing the solvent under reduced pressure the crude product was dried in vacuo and purified by HPLC (Waters RCM, Prep Nova-Pak HR Silica, 25 mm×100 mm) using 8:4:1 hexane:t-butylmethylether:acetonitrile to afford 71.2 mg (71%) of the title compound as a white solid; $^1$H NMR (CDCl₃) δ 1.5 (d, 3H, J=8.6 Hz, C29-H), 2.4 (m, 1H, C20-H); 5.67 (1H, C4-H), 7.40–7.43 (m, 2H), 7.72 (dd, 1H, J=2.2, 6.9 Hz), 7.78 (dd, 1H, J=2.3, 6.9 Hz); Mass Spectrum (APCI) m/e 948, 950 ($^{79}$Br—M+NH₄, $^{81}$Br—M+NH₄).

Step D 4-(2-Bromobenzoyl)oxy-6,7,15,16-tetrakis(acetyloxy)-18-hydroxy-22-methoxycarbonyl[6α,7α,15β,16β,20α]D:A-Friedo-A-homo-27,30-dinor-24-oxaoleana-1,21-dien-3-one

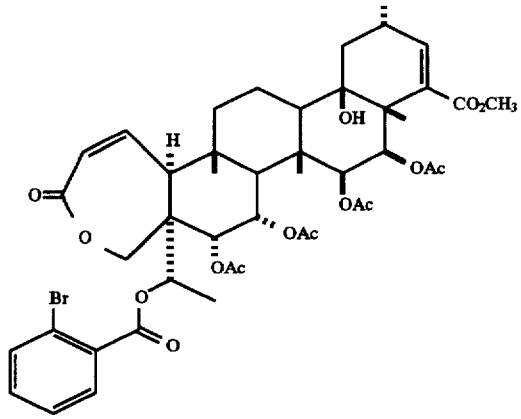

This compound is prepared from 4-(2-bromobenzoyl)oxy-6,7,15,16-tetrakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-en-3-one using the procedures described in Example 8.

EXAMPLE 12

4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one

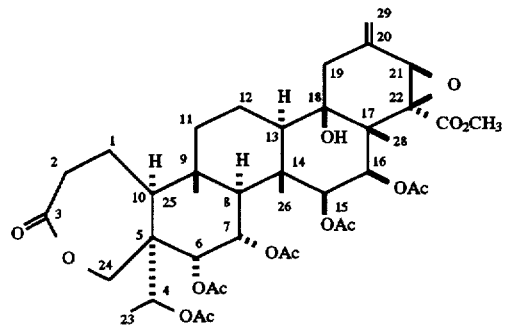

As described in Scheme I, 4,5,6,15,16-pentakis(acetyloxy)-21,22-epoxy-18-hydroxy-22-methoxycarbonyl[6α,7α,15β,16β,21β,22β]D:A-Freido-A-homo-27,30-dinor-24-oxaoleana-1,20(29)-dien-3-one, isolated from *Spachea correa* in liquid ammonia with lithium metal will result in the reduction of the C1 olefin group to produce the saturated lactone.

EXAMPLE 13

4,6,7,15,16-Pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one

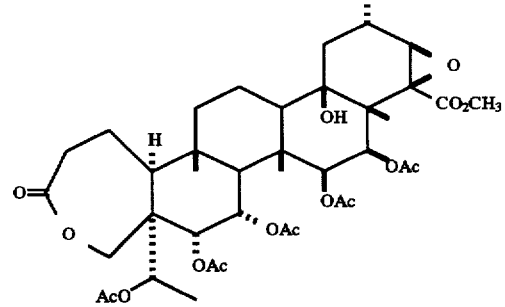

A solution of 50 mg (63.7 μmole) of 4,6,7,15,16-Pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one in 50 ml of dry THF is degassed under reduced pressure and saturated with nitrogen, the procedure being repeated several times. 25 mg of Wilkinson's catalyst [(PPh₃)₃RhCl] are added and the solution is degassed and saturated with hydrogen in the previously described manner. The reaction vessel is then pressurized with $H_2$ to 15 psi (1 atm) and shaken for 65 h at 25° C. After that time the solvent is removed under reduced pressure. The residue is dissolved in a small amount of ethyl acetate/hexanes (2:1) (ca. 1 mL) and filtered through 30 g of silica gel eluting with 500 ml of ethyl acetate/hexanes (2:1). The first fractions, containing the Wilkinson-catalyst (approx. 50 mL) is discarded. The fractions containing the product is combined. After removing the solvent under reduced pressure the crude product is dried in vacuo and purified by HPLC to produce the title compound.

EXAMPLE 14

4,6,7,15,16-Pentakis(acetyloxy)-18-hydroxy-22-methoxycarbonyl[6α,7α,15β,16β,20α]D:A-Friedo-A-homo-27,30-dinor-24-oxaoleana-21-en-3-one

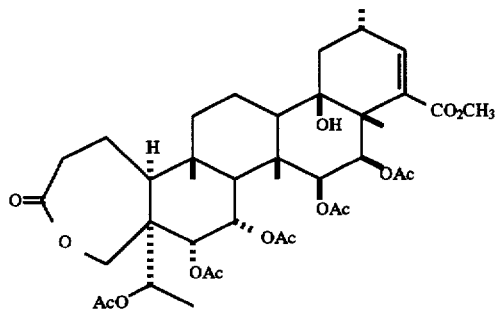

A solution of 48.2 mg (0.104 mmole) of tungsten hexachloride in 8 mL of dry tetrahydrofuran is cooled to −78° C. under nitrogen. Then 0.152 mL (0.208 mmole) of 1.6M butyllithium is added and the solution is allowed to warm to room temperature over 30 min. Then a solution of 20.2 mg (0.026 mmole) of 4,6,7,15,16-Pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one in 2 mL of dry tetrahydrofuran is added and the solution is heated under nitrogen at 50° C. for 18 h. The mixture is applied to a 10 cm column of silica gel, which is washed with 2:1 ethyl acetate-hexane. The eluate is concentrated and purified by silica gel chromatography with 2:1 ethyl acetate-hexane to produce the title compound.

EXAMPLE 15

4,6,7,15,16-Pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaolean

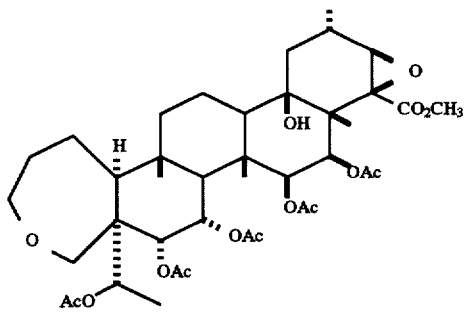

A solution of 213 mg (0.27 mmole) of 4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one in 2 mL of dichloro-methane is cooled to 0° C. Then 0.68 mL of a 1.02M solution of lithium tri-tertbutoxyaluminum hydride is added and the solution is stirred at 0° C. for 18 h. The reaction is quenched with 10 mL of 2.5M aqueous $H_2SO_4$ and then is diluted with 50 mL of dichloromethane. After the layers are separated, the organic phase is dried over $Na_2SO_4$ and concentrated.

The residue is dissolved in a mixture of 5 mL of dichloro-methane and 1 mL of triethylsilane. Then 0.8 mL of boron trifluoride-etherate is added and the solution is stirred at room temperature. After 2 h, the reaction is quenched by addition of saturated aqueous $NaHCO_3$ solution and dichloromethane. The layers are separated and the organic layer is washed with and brine, saturated aqueous $NaHCO_3$, dried over $MgSO_4$, and concentrated. The residue is purified by silica gel chromatography using S (hexane:t-butylmethylether:acetonitrile 8:4:1 ) to produce the title compound.

EXAMPLE 16

4,6,7,15,16-Pentakis(acetyloxy)-18-hydroxy-22-methoxycarbonyl[6α,7α,15β,16β,20α]D:A-Friedo-A-homo-27,30-dinor-24-oxaoleana-21-ene

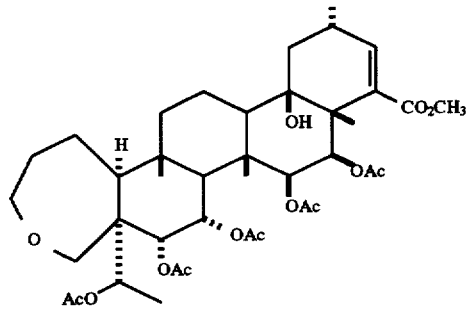

A solution of 233 mg (0.56 mmole) of tungsten hexachloride in 8 mL of dry tetrahydrofuran is cooled to −78° C. under nitrogen. Then 0.70 mL (1.12 mmole) of 1.6M butyl-lithium is added and the solution is allowed to warm to room temperature over 30 min. Then a solution of 111 mg (0.141 mmole) of 4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaolean in 2 mL of dry tetrahydrofuran is added and the solution is heated under nitrogen at 50° C. for 18 h. The mixture is applied to a 10 cm column of silica gel, which was washed with 2:1 ethyl acetate-hexane. The eluate is concentrated and purified by silica gel chromatography with 2:1 ethyl acetate-hexane to produce the title compound.

EXAMPLE 17

4,6,7,15,16-pentakis(acetyloxy)-18-hydroxy-22-methoxycarbonyl[6α,7α,15β,16β]D:A-Friedo-A-homo-27,30-dinor-24-oxaoleana-20(29),21-dien-3-one

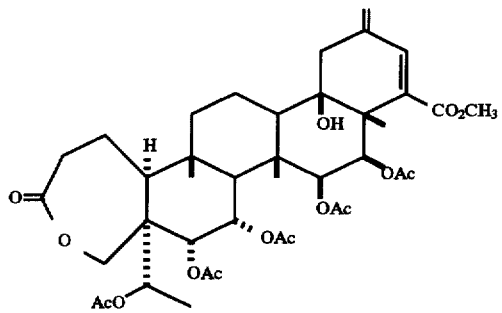

A solution of 233 mg (0.56 mmole) of tungsten hexachloride in 8 mL of dry tetrahydrofuran is cooled to −78° C. under nitrogen. Then 0.70 mL (1.12 mmole) of 1.6M butyllithium is added and the solution is allowed to warm to room temperature over 30 min. Then a solution of 111 mg (0.141 mmole) of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one in 2 mL of dry tetrahydrofuran is added and the solution is heated under nitrogen at 55° C. for 14 h. The mixture is applied to a 10 cm column of silica gel, which is washed with 2:1 ethyl acetate-hexane. The eluate is concentrated and purified by silica gel chromatography with 2:1 ethyl acetate-hexane to produce the title compound.

EXAMPLE 18

4,6,7,15,16-pentakis(acetyloxy)-18-hydroxy-22-methoxycarbonyl[6α,7α,15β,16β]D:A-Friedo-A-homo-27,30-dinor-24-oxaoleana-21-en-3,20-dione

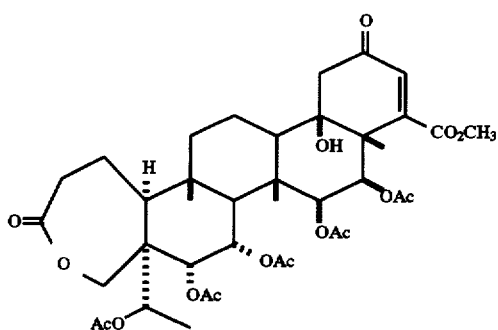

A solution of 120.5 mg of 4,6,7,15,16-pentakis(acetyloxy)-18-hydroxy-22-methoxycarbonyl[6α,7α,15β,16β,21β,22β]D:A-Friedo-A-homo-27,30-dinor-24-oxaoleana-20(29),21-dien-3-one in 40 ml of (1:1, CH$_2$Cl$_2$/CH$_3$OH) is cooled to −78° C. and O$_3$ is bubbled into the solution until it contained a blue color. The solution is then purged with nitrogen for 3 minutes and 0.3 ml of Me$_2$S is added. The solution is allowed to warmed to 25° C. for 14 hours. Volitiles are removed by vaccum and the residue is purified by chromatography on silica gel using 25% ethyl acetate-hexane to produce the title compound.

EXAMPLE 19

4-(2-Bromobenzoyloxy)-6,7,15,16-tetrakis(acetyloxy)-18-hydroxy-22-methoxycarbonyl[6α,7α,15β,16β,20α]D:A-Friedo-A-homo-27,30-dinor-24-oxaoleana-21-en-3-one

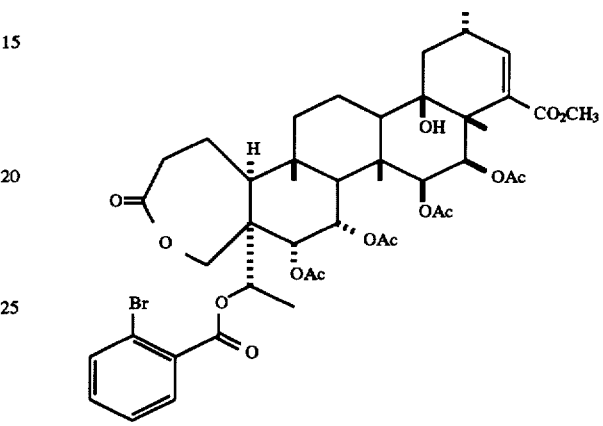

Step A 6,7,15,16-Tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one

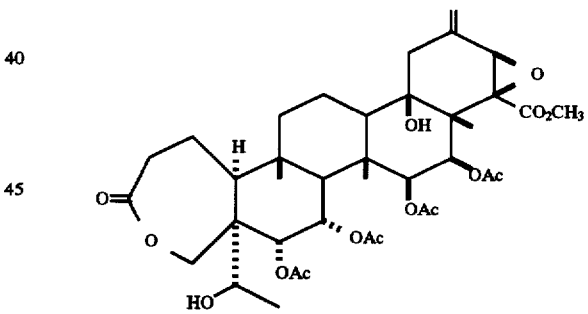

A solution of 4,6,7,15,16-pentakis(acetyloxy)-21,22-epoxy-18-hydroxy-22-methoxycarbonyl[6α,7α,15β,16β,21β,22β]D:A-Friedo-A-homo-27,30-dinor-24-oxaoleana-20(29)-en-3-one in 4 mL of tetrahydrofuran and 2 mL of 3M aqueous HCl is heated at 40° C. for 24 h. The solution is diluted with dichloromethane and the layers are separated. The organic layer is washed with 0.1M phosphate buffer (pH 7), then is dried over MgSO$_4$ and concentrated. The residue was purified by silica gel chromatography with 2:1 ethyl acetate-hexane to produce the title compound.

Step B 4-(2-Bromobenzoyloxy)-6,7,15,16-tetrakis
(acetyloxy)-21,22-epoxy-18-hydroxy-22-
methoxycarbonyl[6α,7α,15β,16β,21β,22β]D:A-
Friedo-A-homo-27,30-dinor-24-oxaoleana-20(29)-
en-3-one

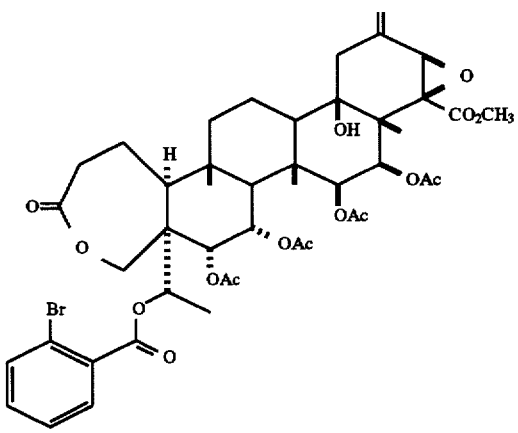

To a solution of 6,7,15,16-tetrakis(acetyloxy)-21,22-epoxy-4,18-dihydroxy-22-methoxycarbonyl[6α,7α,15β,16β,21β,22β]D:A-Friedo-A-homo-27,30-dinor-24-oxaoleana-20(29)-en-3-one in 0.5 mL pyridine is added 27.5 mL (237 µmole) of benzoyl chloride. The solution is stirred at room temperature for 4 h, then is concentrated under reduced pressure. The residue is first filtered through a plug of silica gel and then purified by HPLC (Waters RCM, µ Porosil, 10 mm×10 cm) using a mixture of 9.6:6 (5:4:1 hexane-methyl tert-butyl ether-acetonitrile:hexane) to produce the title compound.

Step C 4-(2-Bromobenzoyloxy)-6,7,15,16-tetrakis
(acetyloxy)-21,22-epoxy-18-hydroxy-22-
methoxycarbonyl[6α,7α,15β,16β,20α,21β,22β]D:A-
Friedo-A-homo-27,30-dinor-24-oxaoleana-3-one

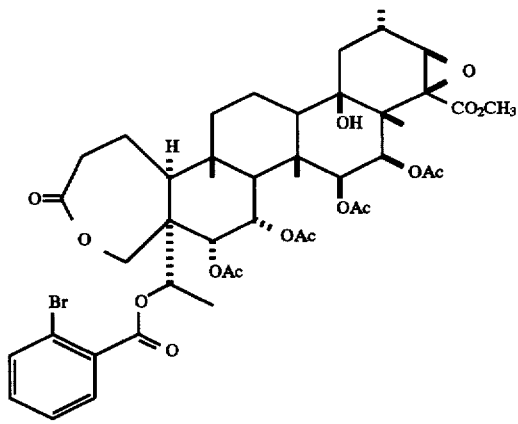

A solution of 4-(2-bromobenzoyloxy)-6,7,15,16-tetrakis (acetyloxy)-21,22epoxy-18-hydroxy-22-methoxycarbonyl [6α,7α,15β,16β,20α,21β,22β]D:A-Friedo-A-homo-27,30-dinor-24-oxaoleana-20(29)-en-3-one in 20 ml of dry THF is degassed under reduced pressure and saturated with nitrogen, the procedure being repeated several times. Then 75 mg of Wilkinson's catalyst [(PPh₃)₃RhCl] are added and the solution is degassed and saturated with hydrogen in the previously described manner. The reaction vessel is then pressurized with H₂ to 50 psi (3.5 atm) and shaken for 72 h at 25° C. After that time the solvent is removed under reduced pressure. The residue is dissolved in a small amount of ethyl acetate/hexanes (1:1) (ca. 1 mL) and filtered through 30 g of silica gel eluting with 500 ml of ethyl acetate/ hexanes (1:1). The first fractions, containing the Wilkinson-catalyst (approx. 50 mL) are discarried. The fractions containing the product are combined. After removing the solvent under reduced pressure the crude product is dried in vacuo and purified by HPLC to produce the title compound.

Step D 4-(2-Bromobenzoyloxy)-6,7,15,16-tetrakis
(acetyloxy)-18-hydroxy-22-methoxycarbonyl-[6α,
7α,15β,16β,20α]D:A-Friedo-A-homo-27,30-dinor-
24-oxaoleana-21-en-3-one

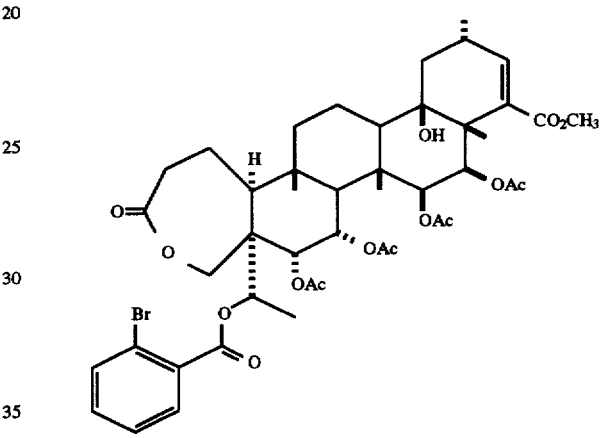

This compound is prepared from 4-(2-bromobenzoyloxy) -6,7,15,16-tetrakis(acetyloxy)-21,22-epoxy-18-hydroxy-22- methoxycarbonyl[6α,7α,15β,16β,20α,21β,22β]D:A-Friedo-A-homo-27,30-dinor-24-oxaoleana-1-en-3one using the procedures described in Example 16.

What is claimed is:

1. A compound of structural Formula I:

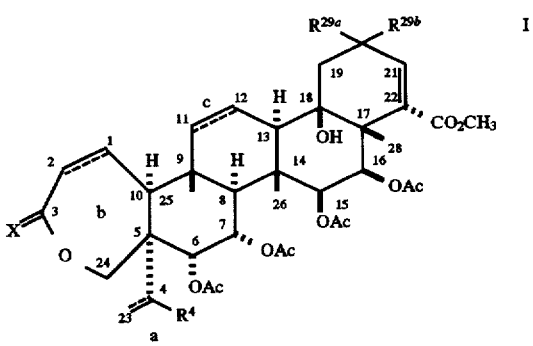

or a pharmaceutically acceptable salt, crystal form or hydrate, wherein:

X is: O, S, NH or H and $R^1$;

a is: a single bond, or a double bond when $R^4$ is absent;

b and c are independently: a single bond or a double bond;

n is: 1 to 4;

m is: 1 to 4;

r is: 0 or 1;

s is: 0 or 1;

$R^1$ and $R^2$ are independently:
  a) H, or
  b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
  a) —$(C_1-C_6)$-alkyl, alkyl as defined above;
  b) —$(C_1-C_6)$-alkenyl, wherein alkenyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;
  c) —$(C_1-C_6)$-alkynyl, wherein alkynyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above,
  d) -aryl, aryl as defined above, or
  e) -heteroaryl, heteroaryl as defined above;

$R^4$ is:
  a) absent and a is a double bond;
  b) —H,
  c) —OH,
  d) =O,
  e) —$O[(C=O)O_r]_sC_1-C_{10}$-alkyl, alkyl as defined above,
  f) —$O[(C=O)O_r]_sC_2-C_{10}$-alkenyl, as defined above,
  g) —$O[(C=O)O_r]_sC_2-C_6$-alkynyl, alkynyl as defined above,
  h) —$O[(C=O)O_r]_s(C_3-C_7)$-cycloalkyl,
  i) —$O[(C=O)O_r]_s$aryl, aryl as defined above,
  j) —$O[(C=O)O_r]_s$heteroaryl, heteroaryl as defined above,
  k) —$O(CH_2)_nO(CH_2)_m$heteroaryl, heteroaryl as defined above,
  l) —$O(CH_2)_nO(CH_2)_m$aryl, aryl as defined above,
  m) —$OC(=O)NR^1R^2$,
  n) —$OSO_2R^3$, or
  o) —$NR^1R^2$;

$R^{29a}$ and $R^{29b}$ are independently:
  a) —H,
  b) =O,
  c) —$(CH_2)_s$—OH,
  d) —$(CH_2)_s NR^1R^2$,
  e) —$(CH_2)_s$—$O[(C=O)O_r]_sC_1-C_{10}$-alkyl, alkyl as defined above,
  f) —$(CH_2)_s$—$O[(C=O)O_r]_sC_2-C_{10}$-alkenyl, alkenyl as defined above,
  g) —$(CH_2)_s$—$O[(C=O)O_r]_s$aryl, aryl as defined above,
  h) —$(CH_2)_s$—$O[(C=O)O_r]_s$heteroaryl, heteroaryl as defined above,
  i) —$(CH_2)_s$—$O(CH_2)_nO(CH_2)_m$heteroaryl, heteroaryl as defined above,
  j) —$(CH_2)_s$—$O(CH_2)_nO(CH_2)_m$aryl, aryl as defined above,
  k) —$(CH_2)_s$—$OC(=O)NR^1R^2$,
  l) —$(CH_2)_s$—$OSO_2R^3$,
  m) —$(C_1-C_6)$-alkyl, alkyl as defined above,
  n) —$(C_2-C_6)$-alkenyl, alkenyl as defined above, or
  o) =$C(C_1-C_{10}$-alkyl$)_2$, alkyl as defined above.

2. The compound of structural Formula I, as recited in claim 1, or a pharmaceutically acceptable salt, crystal form or hydrate, wherein:
  X is: O, S, or NH;
  a is: a single bond;
  b and c are independently: a single bond or a double bond;
  n is: 1 to 4;
  m is: 1 to 4;
  r is: 0 or 1;
  s is: 0 or 1;
  $R^1$ and $R^2$ are independently:
    a) H, or
    b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —$(C_1-C_6)$-alkyl, alkyl as defined above;
b) —$(C_1-C_6)$-alkenyl, wherein alkenyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above;
c) —$(C_1-C_6)$-alkynyl, wherein alkynyl is unsubstituted or substituted with one, two or three substituents selected from the group consisting of: Br, Cl, F, I, $(C_1-C_6)$-alkoxy, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)O_r]_sC_1-C_{10}-alkyl, alkyl as defined above,
f) —O[(C=O)O_r]_sC_2-C_{10}-alkenyl, as defined above,
g) —O[(C=O)O_r]_sC_2-C_6-alkynyl, alkynyl as defined above,
h) —O[(C=O)O_r]_s(C_3-C_7)-cycloalkyl,
i) —O[(C=O)O_r]_saryl, aryl as defined above,
j) —O[(C=O)O_r]_sheteroaryl, heteroaryl as defined above,
k) —O(CH_2)_nO(CH_2)_mheteroaryl, heteroaryl as defined above,
l) —O(CH_2)_nO(CH_2)_maryl, aryl as defined above,
m) —OC(=O)NR^1R^2,
n) —OSO_2R^3, or
o) —NR^1R^2;

$R^{29a}$ and $R^{29b}$ are independently:
a) —H,
b) =O,
c) —(CH_2)_s—O[(C=O)O_r]_sC_1-C_{10}-alkyl, alkyl as defined above,
d) —(CH_2)_s—O[(C=O)O_r]_sC_2-C_{10}-alkenyl, alkenyl as defined above,
e) —(CH_2)_s—O[(C=O)O_r]_sC_2-C_6-alkynyl, alkynyl as defined above,
f) —(CH_2)_s—O[(C=O)O_r]_s(C_3-C_7)-cycloalkyl,
g) —(CH_2)_s—O[(C=O)O_r]_saryl, aryl as defined above,
j) —(CH_2)_s—O[(C=O)O_r]_sheteroaryl, heteroaryl as defined above, i) —(CH_2)_s—O(CH_2)_nO(CH_2)_mheteroaryl, heteroaryl as defined above,
j) —(CH_2)_s—O(CH_2)_nO(CH_2)_maryl, aryl as defined above,
k) —(CH_2)_s—OC(=O)NR^1R^2,
l) —(CH_2)_s—OSO_2R^3,
m) —(C_1-C_6)-alkyl, alkyl as defined above,
n) —(C_2-C_6)-alkenyl, alkenyl as defined above, or
o) =C(C_1-C_{10}-alkyl)_2, alkyl as defined above.

3. The compound of structural Formula I, as recited in claim 2,

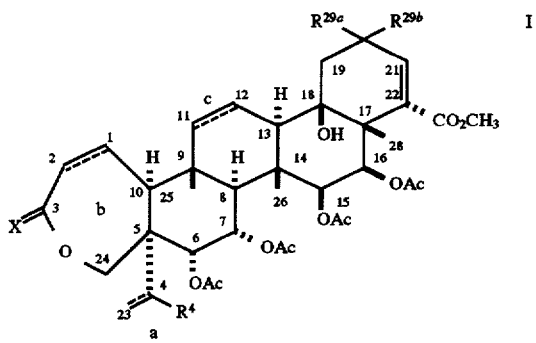

or a pharmaceutically acceptable salt, crystal form or hydrate, wherein:

X is: O;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:
a) H, or
b) $(C_1-C_6)$-alkyl, wherein alkyl is unsubstituted or substituted with one, two or three substituents selected from the group consisting of: Br, Cl, F, I, $(C_1-C_6)$-alkoxy, vinyl, cyano, oxo, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, aryl, wherein aryl is defined as phenyl or naphthyl, unsubstituted or substituted with one, two or three substituents selected from the group consisting of: Br, Cl, F, I, $(C_1-C_6)$-alkoxy, phenyl, phenoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^1R^2$, $NR^1R^2$, $NR^1COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:

a) —($C_1$–$C_6$)-alkyl, alkyl as defined above,
b) -aryl, aryl as defined above, or
c) -heteroaryl, heteroaryl as defined above;

$R^4$ is:
a) —O[(C=O)$O_r$]$_s$$C_1$–$C_{10}$-alkyl, alkyl as defined above,
b) —O[(C=O)$O_r$]$_s$($C_3$–$C_7$)-cycloalkyl,
c) —O[(C=O)$O_r$]$_s$aryl, aryl as defined above,
d) —OC(=O)$O_r$]$_s$heteroaryl, heteroaryl as defined above,
e) —O($CH_2$)$_n$O($CH_2$)$_m$heteroaryl, heteroaryl as defined above,
f) —O($CH_2$)$_n$O($CH_2$)$_m$aryl, aryl as defined above,
g) —OC(=O)$NR^1R^2$, or
h) —$OSO_2R^3$;

$R^{29a}$ and $R^{29b}$ are independently:
a) —H,
b) =O,
c) —($CH_2$)$_s$—O[(C=O)$O_r$]$_s$$C_1$–$C_{10}$-alkyl, alkyl as defined above,
d) —($CH_2$)$_s$—O[(C=O)$O_r$]$_s$$C_2$–$C_{10}$-alkenyl, alkenyl as defined above,
e) —($CH_2$)$_s$—O[(C=O)$O_r$]$_s$$C_2$–$C_6$-alkynyl, alkynyl as defined above,
f) —($CH_2$)$_s$—O[(C=O)$O_r$]$_s$($C_3$–$C_7$)-cycloalkyl,
g) —($CH_2$)$_s$—O[(C=O)$O_r$]$_s$aryl, aryl as defined above,
h) —($CH_2$)$_s$—O[(C=O)$O_r$]$_s$heteroaryl, heteroaryl as defined above,
i) —($CH_2$)$_s$—O($CH_2$)$_n$O($CH_2$)$_m$heteroaryl, heteroaryl as defined above,
j) —($CH_2$)$_s$—O($CH_2$)$_n$O($CH_2$)$_m$aryl, aryl as defined above,
k) —($CH_2$)$_s$—OC(=O)$NR^1R^2$,
l) —($CH_2$)$_s$—$OSO_2R^3$,
m) —($C_1$–$C_6$)-alkyl, alkyl as defined above,
n) —($C_2$–$C_6$)-alkenyl, alkenyl as defined above, or
o) =C($C_1$–$C_{10}$-alkyl)$_2$, alkyl as defined above.

4. The compound of structural Formula I, as recited in claim 3, or a pharmaceutically acceptable salt, crystal form or hydrate, wherein:

$R^4$ is:
a) —O[(C=O)$O_r$]$_s$aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, or
b) —O[(C=O)$O_r$]$_s$heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring.

5. The compound of structural Formula I, as recited in claim 1,

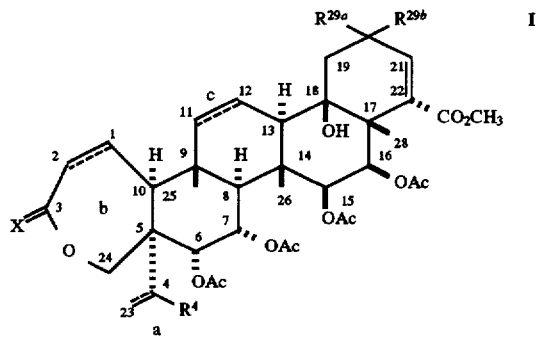

or a pharmaceutically acceptable salt, crystal form or hydrate, wherein:

X is: H and $R^1$;

a is: a single bond;

b and c are independently: a single bond or a double bond;

n is: 1 to 4;

m is: 1 to 4;

r is: 0 or 1;

s is: 0 or 1;

$R^1$ and $R^2$ are independently:
a) H, or
b) ($C_1$–$C_6$)-alkyl, wherein alkyl is unsubstituted or substituted with one, two or three substituents selected from the group consisting of: Br, Cl, F, I, ($C_1$–$C_6$)-alkoxy, vinyl, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —($C_1$–$C_6$)-alkyl, alkyl as defined above;
b) —($C_1$–$C_6$)-alkenyl, wherein alkenyl is unsubstituted or substituted with one, two or three substituents selected from the group consisting of: Br, Cl, F, I, ($C_1$–$C_6$)-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above;
c) —($C_1$–$C_6$)-alkynyl, wherein alkynyl is unsubstituted or substituted with one, two or three substituents selected from the group consisting of: Br, Cl, F, I, ($C_1$–$C_6$)-alkoxy, cyano, oxo, nitro, hydroxy, CHO, $CO_2H$, $COC_1$–$C_6$-alkyl, $CO_2C_1$–$C_6$-alkyl, $CONR^1R^2$, $NR^1R^2$, $NR^1COC_1$–$C_6$-alkyl, aryl as defined above, and heteroaryl as defined above,
d) -aryl, aryl as defined above, or
e) -heteroaryl, heteroaryl as defined above;

$R^4$ is:
a) absent and a is a double bond;
b) —H,
c) —OH,
d) =O,
e) —O[(C=O)O$_r$]$_s$$C_1$–$C_{10}$-alkyl, alkyl as defined above,
f) —O[(C=O)O$_r$]$_s$$C_2$–$C_{10}$-alkenyl, as defined above,
g) —O[(C=O)O$_r$]$_s$$C_2$–$C_6$-alkynyl, alkynyl as defined above,
h) —O[(C=O)O$_r$]$_s$($C_3$–$C_7$)-cycloalkyl,
i) —O[(C=O)O$_r$]$_s$aryl, aryl as defined above,
j) —O[(C=O)O$_r$]$_s$heteroaryl, heteroaryl as defined above,
k) —O(CH$_2$)$_n$O(CH$_2$)$_m$heteroaryl, heteroaryl as defined above,
l) —O(CH$_2$)$_n$O(CH$_2$)$_m$aryl, aryl as defined above,
m) —OC(=O)NR$^1$R$^2$,
n) —OSO$_2$R$^3$, or
o) —NR$^1$R$^2$;

$R^{29a}$ and $R^{29b}$ are independently:
a) —H,
b) =O,
c) —(CH$_2$)$_s$—O[(C=O)O$_r$]$_s$$C_1$–$C_{10}$-alkyl, alkyl as defined above,
d) —(CH$_2$)$_s$—O[(C=O)O$_r$]$_s$$C_2$–$C_{10}$-alkenyl, alkenyl as defined above,
e) —(CH$_2$)$_s$—O[(C=O)O$_r$]$_s$$C_2$–$C_6$-alkynyl, alkynyl as defined above,
f) —(CH$_2$)$_s$—O[(C=O)O$_r$]$_s$($C_3$–$C_7$)-cycloalkyl,
g) —(CH$_2$)$_s$—O[(C=O)O$_r$]$_s$aryl, aryl as defined above,
h) —(CH$_2$)$_s$—O[(C=O)O$_r$]$_s$heteroaryl, heteroaryl as defined above,
i) —(CH$_2$)$_s$—O(CH$_2$)$_s$—O(CH$_2$)$_n$O(CH$_2$)$_m$heteroaryl, heteroaryl as defined above,
j) —(CH$_2$)$_s$—O(CH$_2$)$_n$O(CH$_2$)$_m$aryl, aryl as defined above,
k) —(CH$_2$)$_s$—OC(=O)NR$^1$R$^2$,
l) —(CH$_2$)$_s$—OSO$_2$R$^3$,
m) —($C_1$–$C_6$)-alkyl, alkyl as defined above, or
n) —($C_2$–$C_6$)-alkenyl, alkenyl as defined above, or
o) =C($C_1$–$C_{10}$-alkyl)$_2$, alkyl as defined above.

6. The compound of structural Formula I, as recited in claim 5,

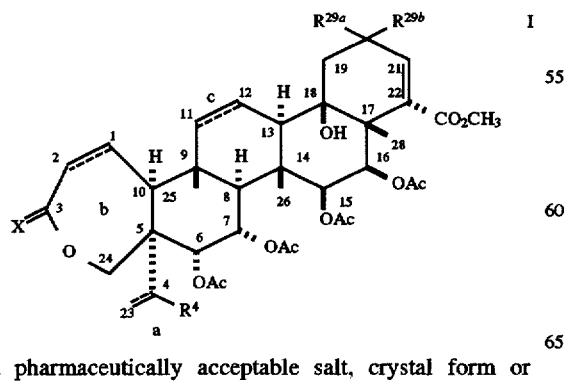

or a pharmaceutically acceptable salt, crystal form or hydrate, wherein:

X is: H and R$^1$;
a is: a single bond;
b and c are independently: a single bond or a double bond;
n is: 1 to 4;
m is: 1 to 4;
r is: 0 or 1;
s is: 0 or 1;

$R^1$ and $R^2$ are independently:
a) H, or
b) ($C_1$–$C_6$)-alkyl, wherein alkyl is unsubstituted or substituted with one, two or three substituents selected from the group consisting of: Br, Cl, F, I, ($C_1$–$C_6$)-alkoxy, vinyl, cyano, oxo, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, aryl, wherein aryl is defined as phenyl or naphthyl, unsubstituted or substituted with one, two or three substituents selected from the group consisting of: Br, Cl, F, I, ($C_1$–$C_6$)-alkoxy, phenyl, phenoxy, cyano, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl and any two of adjacent substituents can be joined to form a 5-, 6- or 7-membered fused ring said ring containing 1 or 2 oxygen atoms and the remainder carbon atoms, heteroaryl, wherein heteroaryl is defined as a 5 or 6-membered ring substituted with one and two heteroatoms selected from O, S, N, unsubstituted or substituted with one, two or three substituents selected from the group consisting of: Br, Cl, F, I, ($C_1$–$C_6$)-alkoxy, cyano, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring;

$R^3$ is:
a) —($C_1$–$C_6$)-alkyl, alkyl as defined above;
b) —($C_1$–$C_6$)-alkenyl, wherein alkenyl is unsubstituted or substituted with one, two or three substituents selected from the group consisting of: Br, Cl, F, I, ($C_1$–$C_6$)-alkoxy, cyano, oxo, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, aryl as defined above, and heteroaryl as defined above;
c) —($C_1$–$C_6$)-alkynyl, wherein alkynyl is unsubstituted or substituted with one, two or three substituents selected from the group consisting of: Br, Cl, F, I, ($C_1$–$C_6$)-alkoxy, cyano, oxo, nitro, hydroxy, CHO, CO$_2$H, COC$_1$–C$_6$-alkyl, CO$_2$C$_1$–C$_6$-alkyl, CONR$^1$R$^2$, NR$^1$R$^2$, NR$^1$COC$_1$–C$_6$-alkyl, aryl as defined above, and heteroaryl as defined above,
d) -aryl, aryl as defined above, or
e) -heteroaryl, heteroaryl as defined above;

$R^4$ is:
a) —OH,
b) —O[(C=O)O$_r$]$_s$$C_1$–$C_{10}$-alkyl, alkyl as defined above,
c) —O[(C=O)O$_r$]$_s$($C_3$–$C_7$)-cycloalkyl,
d) —O[(C=O)O$_r$]$_s$aryl, aryl as defined above,
e) —OC(=O)O$_r$]$_s$heteroaryl, heteroaryl as defined above,
f) —O(CH$_2$)$_n$O(CH$_2$)$_m$heteroaryl, heteroaryl as defined above, g) —O(CH$_2$)$_n$O(CH$_2$)$_m$aryl, aryl as defined above,
h) —OC(=O)NR$^1$R$^2$, or
i) —OSO$_2$R$^3$;

R$^{29a}$ and R$^{29b}$ are independently:
a) —H,
b) =O,
c) —(CH$_2$)$_s$—O[(C=O)O$_r$]$_s$C$_1$–C$_{10}$-alkyl, alkyl as defined above,
d) —(CH$_2$)$_s$—O[(C=O)O$_r$]$_s$C$_2$–C$_{10}$-alkenyl, alkenyl as defined above,
e) —(CH$_2$)$_s$—O[(C=O)O$_r$]$_s$C$_2$–C$_6$-alkynyl, alkynyl as defined above,
f) —(CH$_2$)$_s$—O[(C=O)O$_r$]$_s$(C$_3$–C$_7$)-cycloalkyl,
g) —(CH$_2$)$_s$—O[(C=O)O$_r$]$_s$aryl, aryl as defined above,
h) —(CH$_2$)$_s$—O[(C=O)O$_r$]$_s$heteroaryl, heteroaryl as defined above,
i) —(CH$_2$)$_s$—O(CH$_2$)$_n$O(CH$_2$)$_m$heteroaryl, heteroaryl as defined above,
j) —(CH$_2$)$_s$—O(CH$_2$)$_n$O(CH$_2$)$_m$aryl, aryl as defined above,
k) —(CH$_2$)$_s$—OC(=O)NR$^1$R$^2$,
l) —(CH$_2$)$_s$—OSO$_2$R$^3$,
m) —(C$_1$–C$_6$)-alkyl, alkyl as defined above,
n) —(C$_2$–C$_6$)-alkenyl, alkenyl as defined above, or
o) =C(C$_1$–C$_{10}$-alkyl)$_2$, alkyl as defined above.

7. A compound selected from the group consisting of:

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-en-3-one;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-1,21-dien-3-one;

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-1-ene;

4,6,7,15,16-pentakis(acetyloxy)-18-hydroxy-22-methoxycarbonyl[6α,7α,15β,16β,20α]D :A-Friedo-A-homo-27,30-dinor-24-oxaoleana-1,21-diene;

4,6,7,15,16-pentakis(acetyloxy)-18-hydroxy-22-methoxycarbonyl[6α,7α,15β,16β]D:A-Friedo-A-homo-27,30-dinor-24-oxaoleana-1,20(29),21-trien-3-one;

4,6,7,15,16-pentakis(acetyloxy)-18-hydroxy-22-methoxycarbonyl[6α,7α,15β,16β]D:A-Friedo-A-homo-27,30-dinor-24-oxaoleana-1,21-dien-3,20-dione;

4-(2-bromobenzoyl)oxy-6,7,15,16-tetrakis(acetyloxy)-18-hydroxy-22-methoxycarbonyl[6α,7α,15β,16β,20α]:A-Friedo-A-homo-27,30-dinor-24-oxaoleana-1,21-dien-3-one;

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-21-en-3-one;

4,6,7,15,16-pentakis(acetyloxy)-21,22-epoxy-18-hydroxy-22-methoxycarbonyl[6α,7α,15β,16β,20α,21β,22β]D:A-Friedo-A-homo-27,30-dinor-24-oxaolean;

4,6,7,15,16-pentakis(acetyloxy)-18-hydroxy-22-methoxycarbonyl[6α,7α,15β,16β,20α]D:A-Friedo-A-homo-27,30-dinor-24-oxaoleana-21-ene;

4,6,7,15,16-pentakis(acetyloxy)-18-hydroxy-22-methoxycarbonyl[6α,7α,15β,16β]D:A -Friedo-A-homo-27,30-dinor-24-oxaoleana-20(29),21-dien-3-one;

4,6,7,15,16-pentakis(acetyloxy)-18-hydroxy-22-methoxycarbonyl[6α,7α,15β,16β]D:A-Friedo-A-homo-27,30-dinor-24-oxaoleana-21-en-3,20-dione;

4-(2-bromobenzoyl)oxy-6,7,15,16-tetrakis(acetyloxy)-18-hydroxy-22-methoxycarbonyl[6α,7α,15β,16β,20α]D:A-Friedo-A-homo-27,30-dinor-24-oxaoleana-21-en-3-one;

4-(2-bromobenzoyl)oxy-6,7,15,16-tetrakis(acetyloxy)-21,22-epoxy-18-hydroxy-22-methoxycarbonyl[6α,7α,15β,16β,20α,21β,22β]D:A-Friedo-A-homo-27,30-dinor-24-oxaoleana-3-one.

8. A method of treating a condition in a mammal, the treatment of which is effected or facilitated by K$_v$1.3 inhibition, comprising the administration, in an amount that is effective at inhibiting K$_v$1.3, of a compound of Formula I.

9. The method of treating a condition in a mammal the treatment of which is effected or facilitated by K$_v$1.3 inhibition, as recited in claim 8, wherein the condition is selected from the group consisting of: resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B$_4$-mediated diseases, Coeliac diseases, proctitis, eosinophilic gastmenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-BarMeniyndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infarction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins), lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

10. The method as recited in claim 9, wherein the condition is an autoimmune disease.

11. A method of preventing or treating the resistance to transplantation or transplantation rejection of organs or tissues into a patient in need thereof, which comprises the administration of a compound of claim 1.

12. A method of suppressing the immune system in a subject in need thereof, which comprises the administration to the subject of an immune suppressing amount of a compound of Formula I, as recited in claim 1.

13. A pharmaceutical formulation comprising a pharmaceutically acceptable carrier and a therapeutically effective amount of the compound of Formula I, as recited in claim 1 or a pharmaceutically acceptable crystal form or hydrate thereof.

14. The pharmaceutical formulation of claim 13, comprising in addition, a second immunosuppressive agent comprises azathioprine, brequinar sodium, deoxyspergualin, mizaribine, mycophenolic acid morpholino ester, cyclosporin, FK-506 and rapamycin.

15. The method of claim 12, comprising the coadministration of a second immunosuppressive agent.

16. A method of preventing or treating the resistance to transplantation or transplantation rejection of organs or tissues into a patient in need thereof, which comprises the administration of a compound of claim 1.

17. A method of preventing or treating resistance by transplantation of organs or tissue, graft-versus-host diseases brought about by medulla ossium transplantation; rheumatoid arthritis, systemic lupus erythematosus, Hashimoto's thyroidiris, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infarction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins), lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders which comprises the administration of a compound of claim 1.

18. A method of treating a condition in a mammal, the treatment of which is effected or facilitated by $K_v1.3$ inhibition, comprising the administration of a pharmaceutical formulation comprising a pharmaceutical carrier and a compound of Formula I, as recited in claim 1, in an amount that is effective at inhibiting $K_v1.3$.

19. A method of treating a condition in a mammal, the treatment of which is effected or facilitated by $K_v1.3$ inhibition, comprising the coadministration of a therapeutically effective amount of a compound of Formula I, as recited in claim 1, and a second immunosuppressive agent.

* * * * *